(12) United States Patent
O'Sullivan et al.

(10) Patent No.: US 11,426,556 B2
(45) Date of Patent: Aug. 30, 2022

(54) CATHETER SECUREMENT DEVICE

(71) Applicant: University of Limerick, Limerick (IE)

(72) Inventors: Aidan G. O'Sullivan, Tralee (IE); Leonard W. O'Sullivan, Clonlara (IE); Austin Stack, Limerick (IE); Niall Deloughry, Limerick (IE)

(73) Assignee: University of Limerick, Limerick (IE)

( * ) Notice: Subject to any disclaimer, the term of this patent is extended or adjusted under 35 U.S.C. 154(b) by 0 days.

(21) Appl. No.: 16/481,282

(22) PCT Filed: Jan. 29, 2018

(86) PCT No.: PCT/EP2018/052107
§ 371 (c)(1),
(2) Date: Jul. 26, 2019

(87) PCT Pub. No.: WO2018/138324
PCT Pub. Date: Aug. 2, 2018

(65) Prior Publication Data
US 2020/0038631 A1 Feb. 6, 2020

(30) Foreign Application Priority Data
Jan. 27, 2017 (EP) .................... 17153603

(51) Int. Cl.
*A61M 25/02* (2006.01)
(52) U.S. Cl.
CPC ....... *A61M 25/02* (2013.01); *A61M 2025/024* (2013.01); *A61M 2025/0246* (2013.01); *A61M 2025/0273* (2013.01); *A61M 2205/0205* (2013.01)

(58) Field of Classification Search
CPC .... A61M 2025/024; A61M 2025/0246; A61M 2025/0273; A61M 2205/0205; A61M 25/02
See application file for complete search history.

(56) References Cited

U.S. PATENT DOCUMENTS

| | | |
|---|---|---|
| 7,294,752 B1 | 11/2007 | Propp |
| 2002/0133121 A1 | 9/2002 | Bierman |
| 2007/0043326 A1 | 2/2007 | Navarro et al. |
| 2007/0249980 A1 | 10/2007 | Carrez et al. |
| 2011/0118670 A1 | 5/2011 | Kay et al. |
| 2012/0203182 A1 | 8/2012 | Kay et al. |
| 2014/0163515 A1* | 6/2014 | Hyman ................ A61M 25/02 604/500 |

FOREIGN PATENT DOCUMENTS

| | | |
|---|---|---|
| EP | 0 916 361 A1 | 5/1999 |
| GB | 2 344 054 A | 5/2000 |

OTHER PUBLICATIONS

International Search Report for corresponding Application No. PCT/EP2018/052107, dated May 4, 2018 (7 pages).

* cited by examiner

*Primary Examiner* — Deanna K Hall
(74) *Attorney, Agent, or Firm* — Bookoff McAndrews, PLLC

(57) ABSTRACT

A device for securing a catheter, or similar flexible medical tube or medical device to the skin of a patient. The device comprises a planar body (1) at least a lock retainer (5) and a passive retainer (6), both spaced-apart from each other. Furthermore a method of securing a catheter to a patient using a device as described.

19 Claims, 14 Drawing Sheets

CATHETER SECUREMENT DEVICE

FIELD OF THE INVENTION

The current invention relates to a device for securement of a catheter to the body of a patient.

BACKGROUND OF THE INVENTION

Catheter Related Infections (CRIs) are the most common complication associated with catheters such as central venous catheters. CRIs can lead to a number of complications such as entry site infection, tunnel infection, bacteraemia and sepsis. CRIs are caused by microorganisms permeating the bloodstream through either the skin at the catheter insertion site or through the catheter hub. Many health authorities consider the catheter insertion site to be the major portal for microorganisms causing CRIs as microorganisms gain access to the catheter tip by extra luminal migration along the catheter and enter the bloodstream (external to the catheter). However, it has been reported that in long-term indwelling catheters (>100 days) the identification of microorganisms on the internal lumen of the catheter was more than double that of the external insertion site (internal to the catheter). Trauma to the catheter, i.e. pulling or movement on the catheter at the insertion site, can cause injury and delay the healing process. The injured site also can be an ingress point for microorganisms.

In order to combat these problems, catheters are often held in place by dressings or securement devices.

A catheter dressing is placed at the insertion site on the body to provide a protective covering preventing infection or unwanted movement of the catheter. The "gold standard" in the field of catheter dressing is an antimicrobial patch surrounding the entry site of the catheter and secured with a semipermeable transparent film dressing. The type of antimicrobial agent used varies between chlorhexidine gluconate, silver alginate and iodine based patches depending on the hospital procedure and patient compatibility.

Securement devices are traditionally categorised as suture-less securement devices and sutured securement devices. The Revolution Catheter Securement Device (Merit Medical) is a suture-less device designed to help minimise catheter movement and accidental removal. The device is made from non-woven adhesive material and comprises a set of strings, which together secure the catheter in place at the insertion site on the body. It also comprises a shower lid that can be placed over the device to protect the catheter when a user is showering. However, this device provides no antimicrobial benefits at the catheter entry site and is not intended to be used on vascular catheters.

The SecurAcath (Interrad Medical) is an example of a sutured securement device. This device is designed to prevent unexpected dislodgement of a catheter. The device is anchored subcutaneously in the skin surrounding the catheter and comprises a clip which attaches to the line of the catheter to secure it in place. However, this device provides no antimicrobial benefits at the catheter entry site other than protection from potential dislodgement.

Indwelling central venous catheters can be in place for a number of years. Consistent application of traditional dressings can cause contact irritant dermatitis to the skin surrounding the entry site of the catheter. Furthermore, the integrity of these dressings cannot be maintained in a wet environment. Patients are advised to keep dressings dry and out of direct contact with water at all times, which makes maintaining personal hygiene a challenge.

Prior art devices such as those described above can be susceptible to movement relative to the skin when pulled, for example, when accidently tugged while dressing or when accessing the catheter hub for treatment. These devices also require additional dressings to protect from microbial ingress.

US200700433 discloses a device for fixing a catheter to the body of a patient. The device comprises a housing which can be closed by a hard plastic lid. The housing has two chambers. The first chamber is the part of the device through which the outer part of the catheter passes and the second chamber allows the accommodation of the base of the catheter. The nature of the lid of this device means that when the catheter is in the chamber(s) it is secured in place by the pads on the lid which penetrate the chamber(s). There are several drawbacks to this type of device. Firstly, the device is not universal to any catheter regardless of the shape. Furthermore, the device relies on the securing the catheter at the "Y" shape, i.e. point of bifurcation, of the catheter tubing and thus the placement of the device on the patient will depend on where the catheter was placed and how much exposed catheter is present. Therefore, in using this device it would not be possible to place the device, or the securement chamber of the device, directly adjacent to the insertion site of the catheter regardless of placement depth. In addition, this device does not have any passive retainer, so the base of the catheter comprising the hubs is not easily manipulated or accessed by the user without disturbing the entire catheter, if required. Moreover, the lid of this device is not made from a flexible material.

US20120203182 discloses an adhesive layer arrangement for securing a catheter to the body of a patient. One embodiment of this device comprises a hydrocolloid strip to wrap around and secure a catheter and a tube holder in which the catheter is mechanically secured. This device does not comprise a passive retainer and the retainers on the body of the device are not spaced-apart. This means that any force applied at one retainer will spread across a wide surface area and will affect the other retainer. This will allow excessive movement of the catheter tube. Furthermore, removing the catheter from this device would be cumbersome and the strip would likely leave a sticky residue on the catheter which would require removal for aseptic cleaning. US2011/0118670 discloses a similar device with the same disadvantages.

The device of the current invention aims to alleviate one or more of the above problems by providing a combined dressing and a suture-less securement device, with no susceptibility to water or other contaminant ingress to help reduce catheter related infections and contact irritant dermatitis.

SUMMARY OF THE INVENTION

A first aspect of the invention provides a device assembly for securing a catheter to the skin of the patient, the device assembly comprising a lock retainer configured to be attached to the skin of a patient directly adjacent to an insertion site of a catheter and to retain a catheter tube therein, a passive retainer configured to retain a catheter tube therein and attachable on the skin of a patient distal, and spaced-apart, from the lock retainer.

Preferably, the device assembly further comprises a first flexible planar body on which the lock retainer is disposed. Preferably, the device assembly further comprises a second flexible planar body on which the passive retainer is disposed.

Alternatively, the device assembly comprises a flexible planar body comprising a proximal part on which the lock retainer is disposed and a distal part on which the passive retainer is disposed.

Preferably, the first flexible planar body comprises an access channel for receiving at least part of a catheter tube and terminating in an opening for accommodating at least part of a catheter tube.

Preferably, the flexible planar body comprises an access channel for receiving at least part of a catheter tube and terminating in an opening for accommodating at least part of a catheter tube.

Preferably, the lock retainer comprises two interlocking members configured to lock at least part of a catheter tube therein.

Preferably, the lock retainer is selected from the group comprising a lock, a clamp or a fastener.

Typically, the lock retainer is a longitudinal channel configured to apply pressure to the catheter tube such that the retainer fixes or locks the catheter in place.

Preferably, the passive retainer is a retainer that is configured to apply mechanical pressure or force to retain the catheter therein, preferably selected from tension, compression, interference, or friction.

Preferably, the passive retainer is selected from the group comprising an interference fit retainer, a friction fit retainer, a hook, a pin, a moulded living spring and a resilient channel.

Preferably, the part of the catheter tube is a part comprising the catheter hub.

Preferably, the planar body comprises a flexible material selected from the group comprising silicone, a silicone like material and polyurethane.

Preferably, said planar body is bilaterally flexible.

Preferably, the device comprises a removable cover. Preferably, said cover is semipermeable. Preferably, said cover is transparent. Preferably, said cover is flexible.

Typically, said cover comprises semipermeable polyurethane.

Typically, said cover is a bag.

Preferably at least one reinforcing finger is disposed on the lock retainer, on the passive retainer and/or on the flexible planar body. The reinforcing fingers may extend from the base of the retainer and form along the outer edge of the base. Preferably, a plurality of reinforcing fingers is disposed on the proximal part of the planar body. Preferably, each reinforcing finger extends radially from the lock retainer and/or passive retainer.

Preferably at least one reinforcing finger is disposed on the body. Preferably, a plurality of reinforcing fingers is disposed on the proximal part of the body. Preferably, each reinforcing finger extends radially along the body from the lock retainer towards the outer edge of the body.

A device for securing a catheter to the skin of a patient, the device comprising
  a flexible planar body configured to attach to the skin of a patient,
  an access channel for receiving at least part of a catheter tube and terminating in an opening for accommodating at least part of a catheter tube, and,
  two spaced-apart retainers disposed on the planar body and configured to retain a catheter tube therein.

Preferably, an antimicrobial patch is disposed in the opening.

Preferably, the retainer is a passive retainer.

Preferably, the retainer is a lock retainer.

Preferably, the flexible planar body comprises a proximal part having a first retainer disposed thereon and a distal part having a second retainer disposed thereon.

Preferably, the first retainer is a lock retainer and the second retainer is a passive retainer.

Preferably, the lock retainer comprises two interlocking members configured to lock at least part of a catheter tube therein.

Preferably, the lock retainer is selected from the group comprising a lock, a clamp or a fastener.

Preferably, the passive retainer is a retainer that is configured to apply mechanical pressure or force to retain the catheter therein, preferably selected from tension, compression, interference, or friction.

Preferably, the passive retainer is selected from the group comprising an interference fit retainer, a friction fit retainer, a hook, a pin, a moulded living spring and a resilient channel.

Preferably, the part of the catheter tube is a part comprising the catheter hub.

Preferably, the planar body comprises a flexible material selected from the group comprising silicone, a silicone like material and polyurethane.

Preferably, said planar body is bilaterally flexible.

Preferably, the device comprises a removable cover. Preferably, said cover is semipermeable.

Preferably, said cover is transparent. Preferably, said cover is flexible.

Typically, said cover comprises semipermeable polyurethane.

Preferably at least one reinforcing finger is disposed the on body. Preferably, a plurality of reinforcing fingers is disposed on the proximal part of the body. Preferably, each reinforcing finger extends radially along the body from the lock retainer towards the outer edge of the base.

Preferably, a second passive retainer is disposed on the proximal part of the body. Preferably, a lock retainer comprises a plurality of lock retainers.

Preferably, a passive retainer comprises a plurality of passive retainers.

A method of securing a catheter to a patient, comprising the device or device assembly of the invention is also provided.

Preferably, the method includes a step of attaching a lock retainer directly adjacent to an insertion site of a catheter on the body of a patient.

Typically, the method includes a step of fastening or inserting the proximal end of a catheter in a lock retainer.

The method includes a step of attaching a passive retainer distal to the insertion site, and spaced-apart, from the lock retainer.

Typically, the method includes a step of inserting the distal end of a catheter in a passive retainer.

Preferably, the method includes a step of attaching a device of the invention to the body of the patient, in which the proximal end of the device comprising the lock retainer is attached directly adjacent to the insertion site of a catheter on the body of a patient.

Typically, prior to attachment of the device, a catheter is slidably received along the access channel to be accommodated in the opening of the planar body. Typically, the method includes a step of fastening or inserting the proximal end of a catheter in the lock retainer. Typically, the method includes a step of inserting the distal end of a catheter in a passive retainer.

Preferably, the method further includes applying an antimicrobial patch on the patient's skin and around the catheter tube at the insertion site.

Definitions

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The terms "proximal" and "distal" when used herein are used with reference to the insertion site of the medical line or catheter tube in the body of the patient when in use. Proximal is taken to refer to a part of the device, or device assembly, that is adjacent to or overlaying the insertion site of the catheter on the body. Distal is taken to refer to a part of the device, or device assembly, that is situated away from the insertion site.

The "insertion site" when used herein refers to the point on the body of a patient where the catheter is inserted. This is used interchangeably with "entry site".

The term "catheter" when used herein refers to a flexible or rigid tube which can be inserted through an opening into the body. This term is used interchangeably with catheter tube. The catheter may be, but is not limited to, a central venous catheter, a urinary catheter, a line for administration of intravenous fluids or medication, or a chest drain. The device may also be used to secure other devices such as; epicedial pacing wires or similar wires used in cardiovascular procedures, nasogastric tubes or PEG lines. The device may be used to secure any tubular device to the body. The term "catheter" is taken to encompass these devices. A typical sized catheter used in the body ranges from 4 Fr for a cardiology based application to about 20 Fr for a chest drain. In general a "catheter" comprises a proximal part, which is the part of the catheter that extends from the insertion site on the patient's body. The "catheter" comprises a distal part, which is the part of the catheter comprising the "catheter hub(s)".

Typically, the catheter tube is bifurcated at a point. The bifurcated part of the catheter forms the distal part of the catheter. This part may comprise at least two catheter tubes.

The term "catheter hub", when used herein refers to a threaded connection, usually plastic, at the end of the catheter tube located outside the patient's body.

The term "retainer" when used herein refers to a member configured to retain or hold at least part of a catheter tube in position. The retainer may be any mechanical means of fixation. In one embodiment, the retainer is "active" and locks (or secures) the catheter tube in position in such a way that it cannot be readily removed from the retainer when pulled or tugged. This retainer is referred to herein as a "lock retainer". The lock retainer serves to maintain the catheter tube or part thereof in a fixed position with respect to the skin of the patient. Typically, the lock retainer maintains the catheter in position in three axes, along the longitudinal, lateral and transverse planes. The lock retainer maintains a catheter tube in a fixed position with respect to the patient.

In one embodiment, the retainer is "passive" and retains the catheter part in position such that it can be readily removed from the retainer by a user by pulling or by applying a force. The degree of retaining provided by the lock retainer is greater than the degree of retaining provided by the passive retainer. Typically, the passive retainer maintains the catheter position in two axes along the lateral and transverse planes. The passive retainer maintains the catheter tube close to the skin of the patient but allows lateral movement for ease of engagement and disengagement.

The term "interference fit" when used herein refers to a fit between parts in which the external dimension of one part slightly exceeds the internal dimension of the part into which it has to fit. The level of interference between the parts determines whether or not the fit has a loose fit, a light interference fit, or an interference fit.

The term "friction fit" when used herein refers to a fastening between parts which is achieved by friction after the parts are brought together rather than by any other means of fastening.

BRIEF DESCRIPTION OF THE DRAWINGS

The invention will be more clearly understood from the following description of an embodiment thereof, given by way of example only, with reference to the accompanying drawings, in which:

FIG. 14A to 14 C are views of an embodiment of a passive retainer of the device of the invention.

FIG. 14D to 14F are views of the passive retainer as illustrated by FIGS. 8A and 8B.

DETAILED DESCRIPTION OF THE INVENTION

Figure 1:
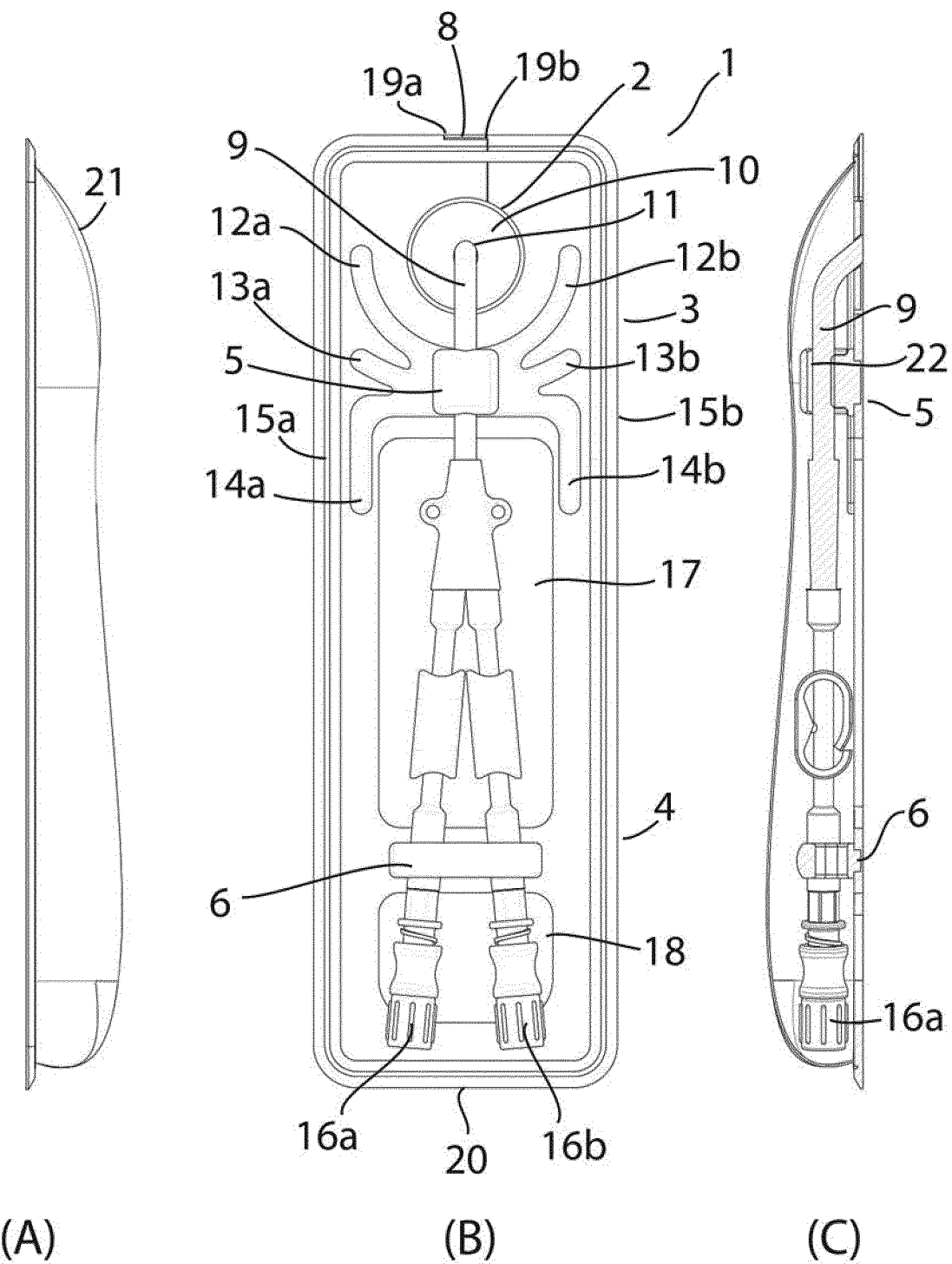
FIG. 1A is a side view of an embodiment of the device of the invention.
FIG. 1B is a front view of an embodiment of the device of the invention.
FIG. 1C is a side view of an embodiment of the device of the invention.

The current invention provides a device for securing a catheter, or similar flexible medical tube or medical device to the skin of a patient. By securing the catheter in place close to the body, the device of the invention reduces the risk of trauma and of accidental damage to the catheter outside of the hospital environment. This in turn reduces the risk of injury and damage to the insertion site which can lead to infection and the necessity to replace a damaged catheter.

The device of the invention also allows the catheter hubs to be easily accessed while maintaining the catheter in place at the insertion site.

The device assembly of the invention comprises a lock retainer configured to attach to the skin of a patient adjacent to the insertion site of a catheter. The lock retainer functions to retain at least part of a catheter tube in place and close to the body of the patient. In an embodiment, the lock retainer is located directly adjacent to the insertion site. Securing the catheter to a lock retainer directly adjacent to the insertion site prevents any unwanted movement of the catheter at this site, thus preventing damage to the catheter or the insertion site.

In an embodiment, directly adjacent is taken to mean placement at about 1 mm to about 40 mm from the insertion site of the patient, typically, about 2 mm to about 30 mm from the insertion site, about 5 mm to about 25 mm, preferably, about 8 mm to about 20 mm from the insertion site, preferably about 10 to about 15 mm.

The lock retainer may be located below the insertion site.

The lock retainer is configured to retain the proximal part of the catheter tube. The lock retainer maintains the catheter tube or part thereof in a fixed position with respect to the skin of the patient.

The device assembly comprises a passive retainer disposable or attachable at a site on the patient's body distal, and spaced-apart, from the lock retainer. The space or distance between the retainers is such that any forces applied at one retainer will be spread across a wide surface area and will not affect the other retainer. This prevents excessive movement of the catheter tubing.

The passive retainer is configured to retain the distal part of the catheter tube. The passive retainer maintains the catheter tube or part thereof close to the skin of the patient but allows lateral movement for easy engagement and disengagement.

In an embodiment, the lock retainer and the passive retainer are configured for attachment to the body of a patient. This may be by any adhesive means as described herein. In one embodiment, the retainers are directly attached to the body of a patient. In one embodiment, the retainers are indirectly attached to the body of a patient by first attaching to a surface, such as the inner surface of a flexible cover. In this embodiment, the cover is then attached to the body of a patient. The cover may be a flexible bag or similar member.

In an embodiment, the lock retainer is disposed or located on a first flexible planar body and the passive retainer is disposed or located on a second flexible planar body. The first and second flexible planar body are attached to the skin of the patient. Alternatively, the first and second flexible planar body are attached to a cover or a bag. The first and second planar body may be any size or shape suitable for the necessary function. The first and second planar body may be adhesive backed. The first and second planar body may be a flexible pad or bandage. They may be made from any suitable material known in the art for use to attach to a patient's skin.

Alternatively, the lock retainer and the passive retainer are disposed on the same flexible planar body. In such an embodiment, the planar body comprises a proximal part and a distal part. The proximal part is the part attachable closest to the insertion site on the patient's body, typically directly adjacent to the insertion site on the patient's body. The lock retainer is disposed on the proximal part and the passive retainer is disposed on the distal part.

The planar body or the retainer may comprise an adhesive surround.

In an embodiment, a lock retainer may include a plurality of lock retainers. In an embodiment, three, four or five lock retainers may be present. In an embodiment, a passive retainer may include a plurality of passive retainers. In an embodiment, three, four or five passive retainers may be present.

The adhesive may be, but is not limited to, a hydrocolloid or a silicone. The adhesive may be applied directly to the attachment surface of the planar body or it may be in the form of a separate adhesive backing or dressing applied to the attachment surface of the planar body.

It will be understood that the adhesive may be any type of pressure sensitive adhesive well known in the art and that is suitable for skin contact. The adhesive is such that the contact irritant dermatitis is reduced. In a preferred embodiment, the adhesive is such that it allows the device to stay in place for up to seven days. This also contributes to the reduction or prevention of contact irritant dermatitis of traditional adhesive dressings.

The device of the invention comprises a flexible planar body. This description herein provided for the flexible planar body may also apply to both the first and/or the second flexible planar body. The planar body is configured to be removably attached to the skin of a patient. Therefore, the device is easy to apply, and replace if necessary, without surgical intervention. This minimises patient discomfort. In use, the planar body of the device is attached adjacent to or overlaying the insertion site of the catheter on the patient's body. The close proximity of the device to the insertion site serves to reduce the risk of accidental dislodgement of the catheter.

The flexible planar body may be any suitable shape or size. In one embodiment, the planar body is elongate. It may be an elongated rectangle. It may be a square or a circle. It will be appreciated that the shape and/or size of the planar body will depend on the intended use of the catheter and the shape and size of the patient's body to which it is to be attached.

In an embodiment, one surface of the planar body (herein after referred to as "the attachment surface") comprises an adhesive for attachment to the skin of the patient. The adhesive may be, but is not limited to, a hydrocolloid or a silicone. The adhesive may be applied directly to the attachment surface of the planar body or it may be in the form of a separate adhesive backing or dressing applied to the attachment surface of the planar body. It will be understood that the adhesive may be any type of pressure sensitive adhesive well known in the art and that is suitable for skin contact. The adhesive is such that the contact irritant dermatitis is reduced. In a preferred embodiment, the adhesive is such that it allows the device to stay in place for up to seven days. This also contributes to the reduction or prevention of contact irritant dermatitis of traditional adhesive dressings.

In one embodiment, the flexible planar body is attached directly to the skin of the patient. In another embodiment, the flexible planar body is attached indirectly to the skin of a patient, by first attaching the inner surface of a flexible cover or bag which is then attached to the body of a patient.

The planar body is flexible. It may be bilaterally flexible. In one embodiment, the planar body comprises a flexible material selected from the group comprising silicone, a silicone like material, polyurethane or a similar flexible material. The planar body may comprise polyurethane foam. It will be appreciated that any suitable flexible material may be used. The flexible nature of the planar body helps to evenly distribute the load and prevents unintentional movement and together with the adhesive, enables the device to attach to the contours of the body. In this way, the catheter can be secured close to the body of the patient.

The planar body may have one or more apertures therein. This increases the flexibility and conformity of the planar body. The apertures may be evenly spaced apart. In one embodiment, the apertures are thin parallel slits. They may extend from an edge of the planar body towards the centre of the planar body. It will be appreciated that the apertures may be any size, shape, number and/or pattern required to provide the necessary level of flexibility and conformity to the device to allow it to fix and align with the contours of the body of the patient.

The planar body comprises an access channel to allow ingress or receipt of at least part of the catheter. In an embodiment in which there is more than one planar body, the access channel may be in the first planar body which comprises the lock retainer. The access channel extends inward from an edge of the planar body typically along the longitudinal axis. The access channel may terminate in an opening or aperture for accommodating at least part of the catheter tube. The opening may be substantially circular in shape. However, it will be understood that any suitable shape may be used.

In an embodiment, the access channel comprises a radial slit extending from the top edge of the proximal part of the body and terminating in an opening for receiving at least part of the catheter tube. In one embodiment, the slit has overlapping edges.

The access channel allows the catheter to be inserted into the opening while simultaneously placing the device over the insertion site without risk of damage or unnecessary movement of the tube. In use, the user pulls the opposing edges of the access channel apart and the catheter tube is slideably received along the access channel and into the opening for accommodating the tube. The body is then secured to the skin of the patient.

One surface of the body, opposite to the attachment surface, (herein after referred to "the mounting surface"), comprises at least two spaced apart retainers disposed thereon. The retainers are configured to retain at least part of the catheter tube in position therein. It will be appreciated that "two" may also include "at least two" or "two or more". In an embodiment, three, four or five retainers may be present on the planar body. It will be understood that the number of retainers depends on the size of the planar body, the intended use of the device and the position of the device on the patient's body.

The description of the retainers as discussed herein applies to all embodiments of the invention. The retainers may be moulded or integral with the planar body or separate discrete parts. The retainers may comprise the same material as the flexible planar body or different.

The two retainers, or the lock and the passive retainers, are disposed on the planar body in such a way that they are spaced-apart. In an embodiment in which the retainers are not present on the same flexible planar body, the retainers are disposed at a position on the patient's body such that they are spaced part. In other words, the retainers are arranged with a space between them. The space or distance between the retainers is such that any forces applied at one retainer will be spread across a wide surface area and will not affect the other retainer. This prevents excessive movement of the catheter tubing. In an embodiment, the space between the first retainer and the second retainer is between 50 mm and 300 mm in length, preferably, 75 mm, 100 mm, 125 mm, 150 mm, 175 mm, 200 mm, 225 mm, 250 mm or 275 mm.

The retainers are configured to retain the catheter or part thereof flush with the surface of the planar body.

The retainer may be a lock retainer. The retainer may be a passive retainer. The two retainers may be the same or different. In an embodiment, the two retainers comprises a first retainer which is a lock retainer and a second retainer which is a passive retainer or vice versa.

The degree of retaining provided by the lock retainer is greater than the degree of retaining provided by the passive retainer.

The lock retainer is configured to lock (or secure) at least part of the catheter tube in position. It will be appreciated that that the lock retainer may be any mechanical member suitable for providing a locking function to secure the catheter tube in position in such a way that the tube cannot be readily removed when pulled or tugged. This enables the catheter to remain motionless, e.g. at the insertion site. This type of retainer limits the movement of the catheter tube in an undesirable direction, i.e., longitudinal, lateral and/or transverse direction, which could lead to dislodgement or damage to the catheter. The locking is reversible. The lock retainer may be selected from the group comprising a lock, a clamp, a fastener or similar member.

In an embodiment, the lock retainer comprises a longitudinal channel that exerts a radial mechanical force inwards towards a catheter placed therein such that it retains the catheter in all directions, i.e. in the longitudinal, lateral and transverse direction.

In an embodiment, the lock retainer comprises a longitudinal channel configured to retain at least part of the catheter tube therein. The retainer maintains the catheter in position as part of the catheter is cradled in the channel. The longitudinal channel is defined between two opposing upstanding walls, or columns, preferably ridged, that extend from a base. The base may form part of, or be attached to, a flexible planar body. The base may be any suitable shape or size. Each wall may comprise cantilevered arm or wing. Typically, the arm extends from the top surface of the wall and substantially parallel to the base. The retainer is accessed by applying force to the cantilevered arms which, when depressed, spreads the channel open to allow the catheter to be place inside the channel. The same action is used to remove the catheter tube from the channel, when necessary. The channel exerts a radial mechanical force inwards once the catheter is placed in the channel and this retains the catheter in all directions, i.e. in the longitudinal, lateral and transverse direction. Preferably, the catheter is retained adjacent to the insertion site on the patient's body. The close proximity to the insertion site serves to reduce the risk of accidental dislodgement of the catheter. Typically, the retainer is a single piece moulded mechanism. In an embodiment, the lock retainer comprises two interlocking members configured to lock at least part of a catheter tube therein.

In an embodiment, the lock retainer comprises a channel configured to retain at least a part of a catheter tube therein and a cap portion mountable thereon and configured to lock the tube in place in the channel.

In an embodiment, the lock retainer comprises a pair of upstanding walls, separated by a base to define a channel therebetween, a pair of opposing groves disposed in the walls of a size to accommodate at least a part of the tube when received therein, and a cap portion mountable thereon and configured to lock the tube in placed when nested in the channel.

The cap portion is configured to enclose the channel therein and comprises a lower abutment surface contacting a point on the base surrounding the walls. In one embodiment, the cap portion is transparent. In such an embodiment, the catheter tubing is pushed into the channel which causes the walls of the channel to move aside for engagement with the tubing. Once the tubing is within the channel, the walls of the channel return towards the original position to accomplish the fit required to latch the components together. The cap portion serves to prevent any movement of the tubing out of the channel.

In an embodiment, the retainer is a passive fit retainer configured to retain or hold at least part of the catheter tube in position in such a way that the tube can be readily removed from the retainer by a user by pulling. This type of retainer allows easy access to the catheter tubing and catheter hubs in use. In an embodiment, the passive retainer is configured to hold part of at least two catheter tubes. It will be understood that the passive retainer may be any suitable retainer capable of providing the necessary function.

In an embodiment, the passive retainer is a retainer that is configured to apply mechanical pressure or force to retain the catheter therein, preferably selected from tension, compression, interference, or friction. The passive retainer is selected from the group comprising an interference fit retainer, a friction fit retainer, a hook, a pin, a moulded living spring and a resilient channel.

The passive retainer may be a hook, a pin or similar member. In such an embodiment, the catheter tube may be wound or looped around the hook or similar member to achieve the fit required to retain the catheter tube in place. The tube may be wound or looped once or a plurality of times, depending on the level of fit required.

One type of passive retainer is a friction fit retainer.

In an embodiment, the passive retainer is generally T shaped.

In an embodiment, the friction fit retainer is a resilient channel configured to retain at least a part of a catheter tube therein. The resilient channel applies mechanical pressure to the catheter tube thereby retaining it in place. Two or more channels may be present in the retainer.

In an embodiment, the passive retainer is configured to hold part of at least two catheter tubes.

Figure 14:
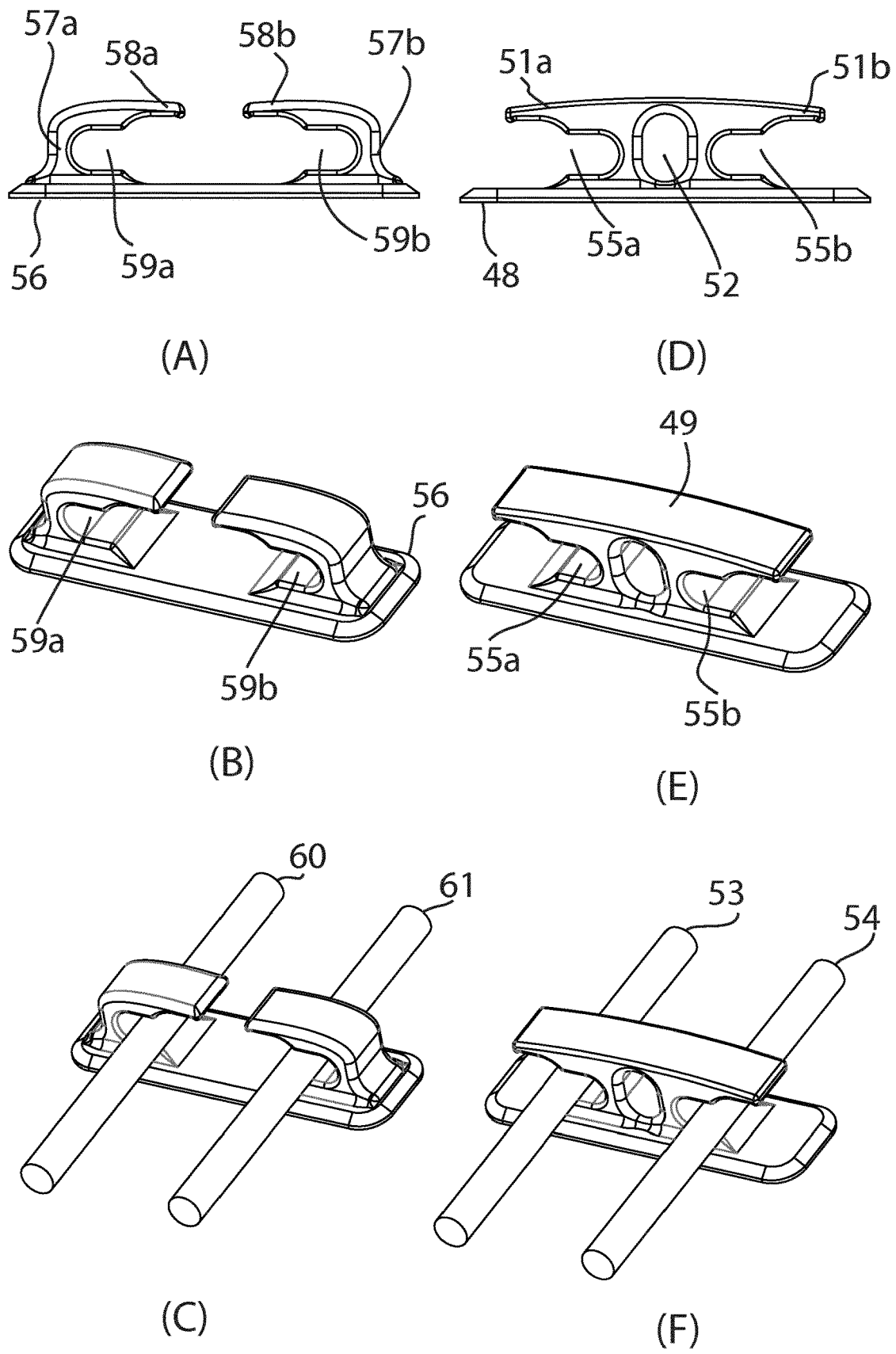
Figure 15:
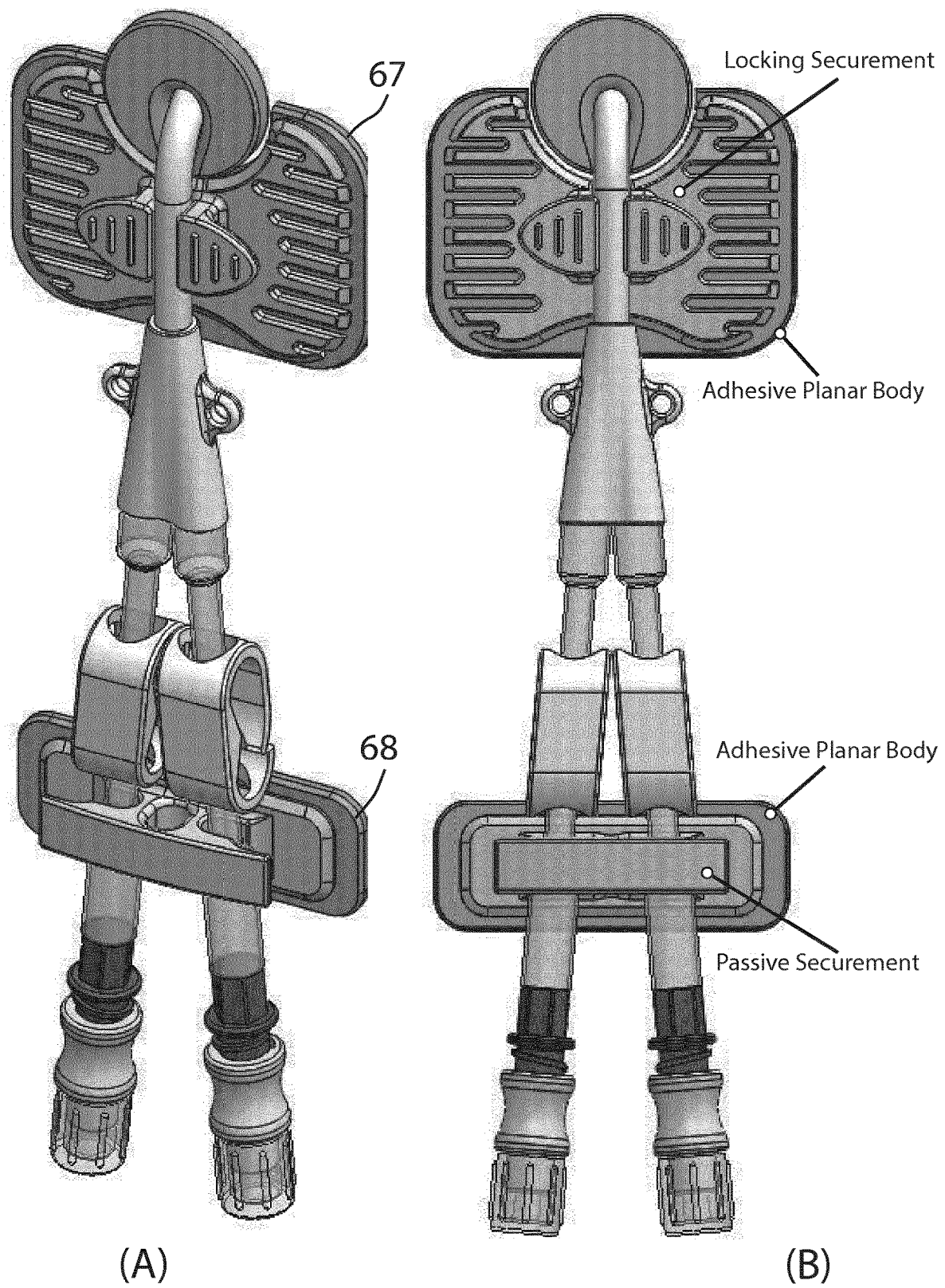
FIG. 15A is a perspective view of an embodiment of the device of the invention.
FIG. 15B is a side view of the device of FIG. 15A.

The friction fit retainer may comprise a base having an upstanding wall, a flange extending outwards at the top surface of the wall and substantially parallel to the base to form a channel therebetween in which the catheter tube is nested or retained in place. The base may be part of, or attached to, a planar body. The wall and flange may be L-shaped in cross section. The wall may comprise a second arm, or flange, extending outwards at the top surface and opposing the first arm, or flange, to form a second channel. The wall and flange(s) together may be T-shaped in cross section. The parts of the friction fit retainer may be made of a flexible material. The flange(s), or arm, may be cantilevered from the wall. The catheter tube or part thereof, can be secured in the channel by moving the tube laterally into place and can be freely accessed by moving the tube from beneath the flange(s) and out of the channel. This retainer provides a compression force to retain the catheter tube between the flange(s) within the channel. The retainer prevents movement of the catheter tubes in the transverse and lateral directions. An example of this embodiment is illustrated by FIG. 14 D to F.

The passive retainer may comprise a base having two opposing upstanding walls at opposing ends (outermost) of the base. Each wall may have a flange, or arm, extending inwards from the wall and towards the centre of the base and parallel to the base. This configuration forms a channel between the arm and the base. In other words, this configuration comprises two opposing channels. The catheter tube or part thereof, can be secured in the channel(s) by moving the tube laterally into place and can be freely accessed by moving the tube from beneath the flange(s) and out of the channel. This retainer provides a compression force to retain the catheter tube between the flange(s) within the channel. The retainer prevents movement of the catheter tubes in the transverse and lateral directions. An example of this embodiment is illustrated by FIG. 14 A to C.

The planer body of the device of the current invention comprises a proximal part and a distal part. As explained, the terms "proximal" and "distal" when used herein are used with reference to the insertion site of the medical line or catheter tube in the body of the patient when in use.

In other words, in use on a patient's body, the proximal part of the planar body is adjacent to or overlays the insertion site of the catheter on the body. The distal part is the part of the planar body distal to the insertion site. Thus, it will be appreciated that the distal part of the planar body is further away from the insertion site than the proximal part of the planar body.

In an embodiment, a first retainer is disposed on the proximal part of the planar body and a second retainer is disposed on the distal part of the planar body. The first and second retainers are spaced apart.

In an embodiment, a lock retainer is disposed on the proximal part of the planar body and a passive retainer is disposed on the distal part of the planar body. Preferably, the lock retainer is directly adjacent to the insertion site. The lock retainer is spaced apart from the passive retainer.

Having a lock retainer at this position prevents unwanted movement of the catheter tubing at the entry site.

As the retainers are spaced apart, any force applied to the catheter near the friction fit retainer or passive retainer, e.g. pulling or movement of the catheter tube is spread across a wide surface area to protect the catheter, in particular, the part of the catheter at the entry site on the body in the lock retainer. This prevents movement of the catheter tubing at the entry site and thus avoids damage or injury to the entry site.

This is particularly beneficial when the passive fit retainer retains the catheter hub, as this allow the hub(s) to be moved and accessed during use without the risk of movement of the catheter tube at the entry site as it is securely held in place by the lock retainer. This removes the risk of accidental damage when used, for example, during dialysis.

The lock retainer and the passive retainer are as described herein.

In a further embodiment, a second passive retainer is disposed on the proximal part of the planer body. The second passive retainer may be disposed in the same plane as the lock retainer. The second passive retainer may be spaced apart from the first passive retainer and/or the lock retainer. This embodiment is particularly beneficial for fitting non-central venous catheters, for example IV-line catheters. The arrangement of the two passive retainers allows the tube to form a U-shape, across the surface of the planar body, thereby keeping the tubing close to the body and preventing any movement while allowing flow within the tubing, e.g. not obstructed by pinching.

In an embodiment, an antimicrobial patch or pad is disposed surrounding the catheter at the insertion site. Preferably, the patch is disposed in the opening. The patch is configured for attachment to the body over the insertion site on the body. It is in direct contact with the insertion site on the patient's body. Preferably, the patch is applied before the planar body of the device. The patch comprises a substantially central aperture for receiving and accommodating at least part of a catheter tube. This central aperture fits around the catheter entry site on the patient's body.

In an embodiment, the patch comprises or is impregnated with, chlorohexidine gluconate, iodine or silver alginate or any suitable agent for for reducing local infections, catheter-related blood stream infections (CRBSI) and skin colonization of microorganisms commonly associated with CRBSI. The patch is removable which allows the use of chlorohexidine gluconate, iodine or silver alginate based patches without the necessity for multiple dressing versions depending on patient specific requirements. The patch is substantially the same size and shape as the opening such that it is perimeter is in sealable engagement with the inner perimeter of the opening. Preferably, the patch is disk. The patch may be a suitable patch known in the art. For example, the patch may be a BIOPATCH® (www.ethicon.com).

At least one reinforcing finger is disposed on the planar body. In one embodiment, a plurality of reinforcing fingers is disposed on the proximal part of the body. Typically, the fingers extend from the retainer, preferably the lock retainer, towards the outer edge of the body. The reinforcing fingers may be integral or moulded with the lock retainer. In an embodiment, the fingers extend radially from the retainer towards the outer edge of the body. The fingers function to disperse any external forces across a larger surface area, reducing trauma to the catheter. The amount, shape and/or placement of the reinforcing fingers is such that that stress is reduce when the body of the device is flexed. Preferably, there are from 1 to 20 reinforcing fingers, preferably, 2, 4, 6, 8, 9, 10, 12, 14, 16 or 18. Preferably, the reinforcing fingers are disposed as opposing pairs of reinforcing fingers. The reinforcing fingers as described herein may be disposed on the base of the retainer(s).

In an embodiment of the invention, the device comprises a removable cover, preferably a substantially transparent cover, overlaying the planar body. The cover may be semi-permeable in that it is permeable to oxygen, carbon dioxide and water vapour but does not allow bacteria and water to pass through. In an embodiment, the cover comprises a thin and flexible material. Typically, the cover comprises polyurethane. The cover may be attached to the device or directly to the patient' body.

The cover forms a barrier between the sterile field of the catheter (Aseptically cleaned in the hospital by medical professionals) and the outside environment. This allows the patient to continue normal activities without concern of water and other pathogen contamination. This reduces the rate of CRIs. The cover also keeps the tubing anchored to the device flush and tight to the contours of the body and reduces the catch risk. From an aesthetic point of view, the device is also more discrete. The cover has a self-adhesive backing. The cover can be attached to the planar body of the device along its outer edge. The cover has a self-adhesive backing, and can be attached along substantially all of the outer edge of the body. Typically, it is adhesive backed.

The cover is removable to allow access to the catheter without the necessity to replace the device. In use, after catheter access the body will be aseptically cleaned and a new cover affixed.

In an embodiment, the removable cover is a bag, or similar member, that covers the entire device. The bag has a single access point at one end, through which the device may be inserted. The bag may be substantially transparent. The bag may be semipermeable in that it is permeable to oxygen, carbon dioxide and water vapour but does not allow bacteria and water to pass through. In an embodiment, the bag comprises a thin and flexible material. Preferably, the bag comprises polyurethane or similar material. In an embodiment, the device or device assembly is placed inside a removable bag. The retainers are attached to the inner surface of the bag. One outer surface of the bag is configured for attachment to the patient's body at the desired location. The bag may be attached by any means as described herein as being suitable for attachment to a patient's body. The advantage of using a cover of this nature is that it reduces the risk of water or pathogen ingress as it completely encompasses the device. In use, once the catheter and device are inserted into the bag, the opening of the bag is sealed onto the patient's skin, preferably around the insertion site. Sealing may be by any adhesive means as described herein.

The current device is compatible with all brands of catheter. This means hospitals will not have to alter their catheter supplier or placement procedures.

In one embodiment, the device of the invention is attached to the patient's body as follows: The user pulls the opposing edges of the access channel apart and the catheter tube that has been placed in the body is slideably received along the access channel and into the opening for accommodating the tube. The planar body of the device is then secured to the skin and the contours of the patient by its adhesive backing. A part of the catheter tubing is then locked to the planar body of the device by the lock retainer that is disposed on the proximal part of the planar body. This serves to secure the catheter tubing and prevent movement of the tubing at the insertion site. A part of the catheter tubing comprising the catheter hub(s) is then placed in the passive retainer that is disposed on the distal part of the planar body distal to the insertion site. This serves to loosely hold the catheter tubing in place such that it can be easily removed and accessed by the user at any time. A cover may be attached over the surface of the device along the perimeter of the planar body. This cover is removeable to allow easy access to the catheter when needed. This cover is water resistant and also prevents any accidental pulling of the catheter tubing, thereby reducing the risk of trauma and of accidental damage to the catheter outside of a hospital environment. This makes living with a catheter more manageable for the patient. This dual locking system allows the catheter to be held securely at the insertion site while the flexible nature of the passive retainer allows the catheter hubs to be accessed without causing unnecessary movement of the catheter. As the retainers are spaced apart any pulling that does occur at the transition fit is spread evenly over the surface of the body such that it prevents movement of the catheter at the insertion site.

The device will now be described with reference to the drawings. The drawings are exemplary only.

FIG. 1 B illustrates an embodiment of the device of the invention. The device comprises an elongated rectangular planar body 1 comprising a flexible silicone-like material. The body has an adhesive backing (not shown). The adhesive backing attaches the planar body to the skin of the patient (not shown). The planar body comprises a proximal part 3, proximal of the catheter insertion site on the body when in use (not shown) and a distal part 4, distal of the insertion site. An access channel 8 in the form of a radial slit with overlapping edges (19a, 19b) extends from the top edge of the proximal part 3 towards the centre of the planar body terminating in an opening 2 for receiving and accommodating at least part of a catheter tube 9. An antimicrobial patch 10 is placed in the opening. The patch is substantially the same size and shape as the opening. The antimicrobial patch 10 comprises a central aperture 11 for receiving the catheter tube 9. In use, the catheter tube 9 is threaded through the aperture 11 on the patch 10 and the patch 10 is attached to the skin of the patient overlaying the insertion site (not shown). In order to fix the device to the patient, the user pulls apart the edges of the access channel and the catheter tube is slidably received through the channel and into the opening. The user then applies pressure to the planar body 1 in order to affix the device to the body of the patient. The proximal part 3 further comprises a lock retainer 5 configured to lock or secure the catheter tube in place at the insertion site. The lock retainer 5 of the embodiment of FIG. 1 comprises a base and two opposing walls (not shown). The walls form a channel into which the catheter tube 9 is nested. The walls comprise opposing groves. A part of the catheter tube inserts and is accommodated in the groves (not shown). The lock retainer 5 comprises a cap portion mounted to enclose the walls and the catheter tube therein. The lower surface of the cap portion contacts the part of the planar body surrounding the walls to secure the catheter in place (not shown) in the channel. Three sets of opposing elongate reinforcing fingers (12a, 12b, 13a, 13b, 14a, 14b) are disposed on the proximal end extending outwards from the lock retainer towards the outer edge 15a, 15b of the planar body 1. The lock retainer 5 is spaced apart from a friction fit retainer 6 positioned distal of the insertion site on the distal part 4 of the body. The friction fit retainer 6 comprises a base and a T-shaped flange extending upwards from the base. The flange forms opposing channels with the base (not shown). The catheter tubes adjacent to the catheter hub 16a, 16b, are retained in the opposing channels. The planar body 1 further comprises an aperture 17 extending between the lock retainer 5 and the friction fit retainer 6. The planar body 1 comprises another aperture 18 extending between the friction fit retainer 6 and the lower edge of the distal part 20.

In use, a part of the catheter tube is locked in place at the insertion site by the lock retainer. A part of the catheter tube having the catheter hubs is held in place by the friction fit retainer. This dual locking system allows the catheter to be held securely at the insertion site while the flexible nature of the friction fit retainer allows the catheter hubs to be accessed without causing unnecessary movement of the catheter. As the retainers are spaced apart any pulling that does occur at the transition fit is spread evenly over the surface of the body such that it prevents movement of the catheter at the insertion site.

FIG. 1 A illustrates a side view of the device of FIG. 1B comprising a cover 21. The cover 21 is positioned over the entire top surface of the planar body to enclose the planar body therein. The cover is attached to the planar body along the entire perimeter of the body.

FIG. 1C illustrates a side cross-sectional view of the device of FIG. 1B comprising a transparent cover 21. The cover is positioned over the entire top surface to enclose the planar body therein. The cover is attached along the entire perimeter of the planar body. The catheter tube 9 inserted into the channel 22 of the lock retainer 5 is illustrated by FIG. 1B.

Figure 2:
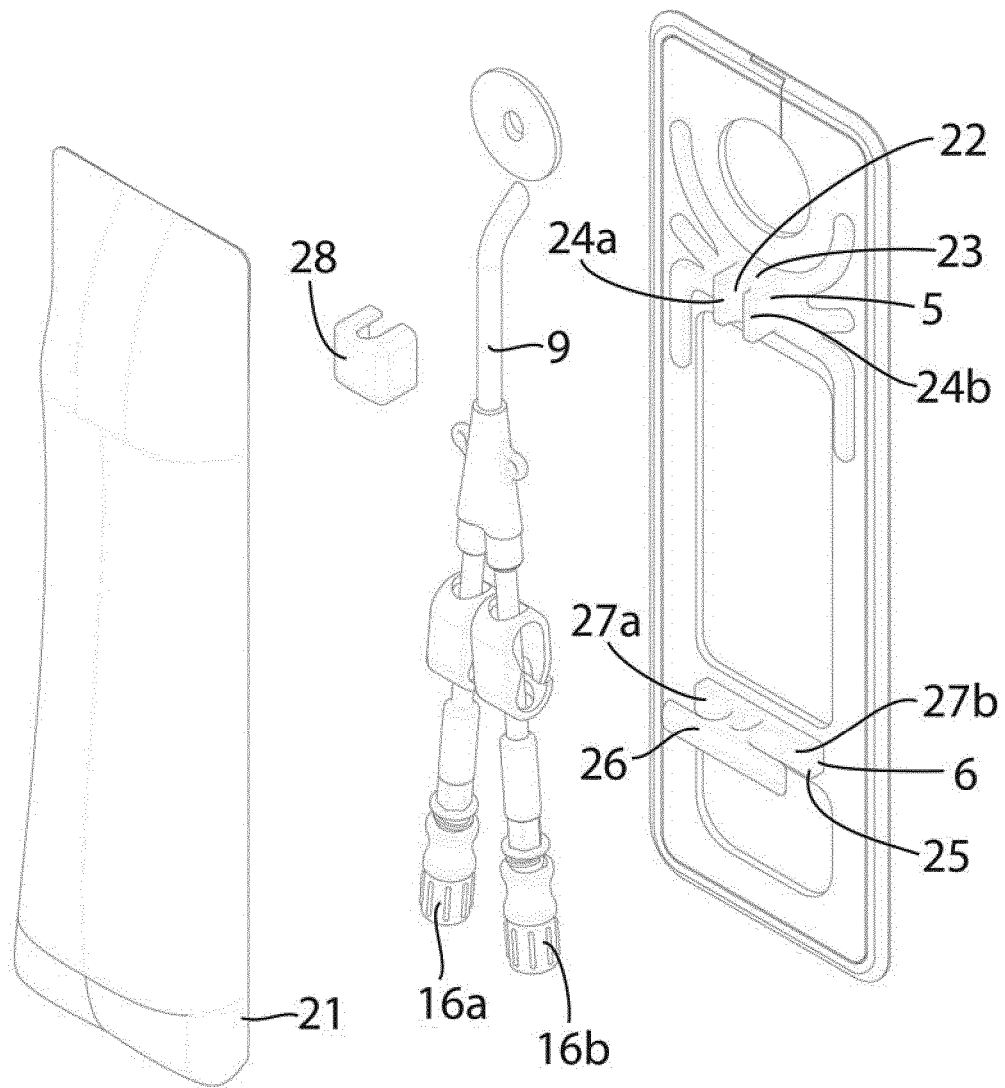
FIG. 2 is an expanded view of the device of FIG. 1.

FIG. 2 is an expanded view of the device of FIG. 1. The lock retainer 5 comprises a base 23 with two opposing and upstanding walls 24a, 24b, forming a channel 22 therebetween. The catheter tube 9 is nested in this channel in use. The friction fit retainer 6 comprises a base 25, with an upstanding T-shaped flange 26. The base and the flange form two opposing channels 27a, 27b therebetween. The catheter tube 9 is nested into the channels in use (not shown). The cap portion 28 may be mounted to secure the walls and the catheter tube therein.

Figure 3:
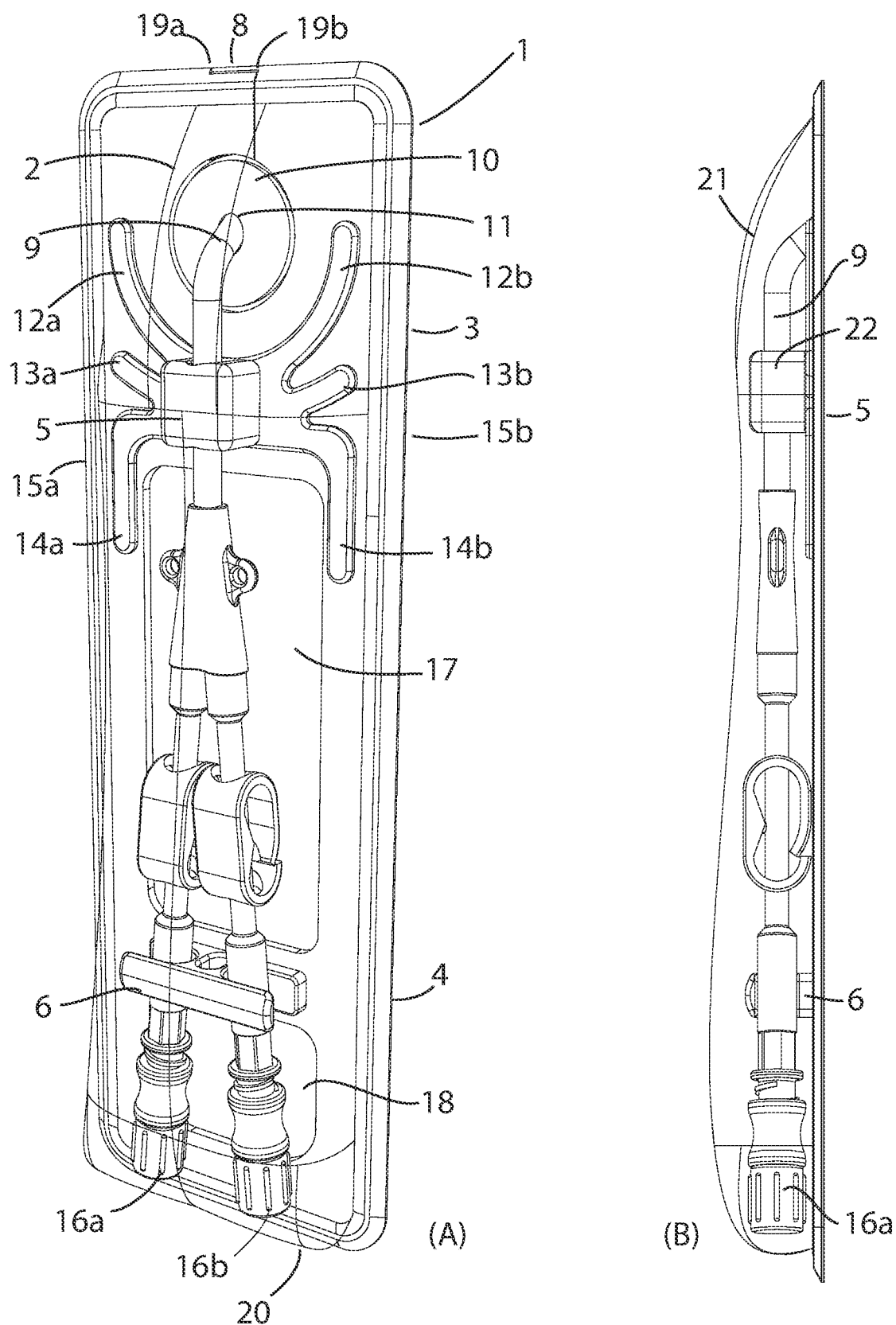
FIG. 3A is a perspective view of the device of FIG. 1.
FIG. 3B is a side view of the device of FIG. 3A.

FIG. 3A is a perspective view of the device of FIG. 1. FIG. 3B is a side view of the device of FIG. 1 In this figure, the tubing within the channels of the retainer is illustrated.

Figure 4:
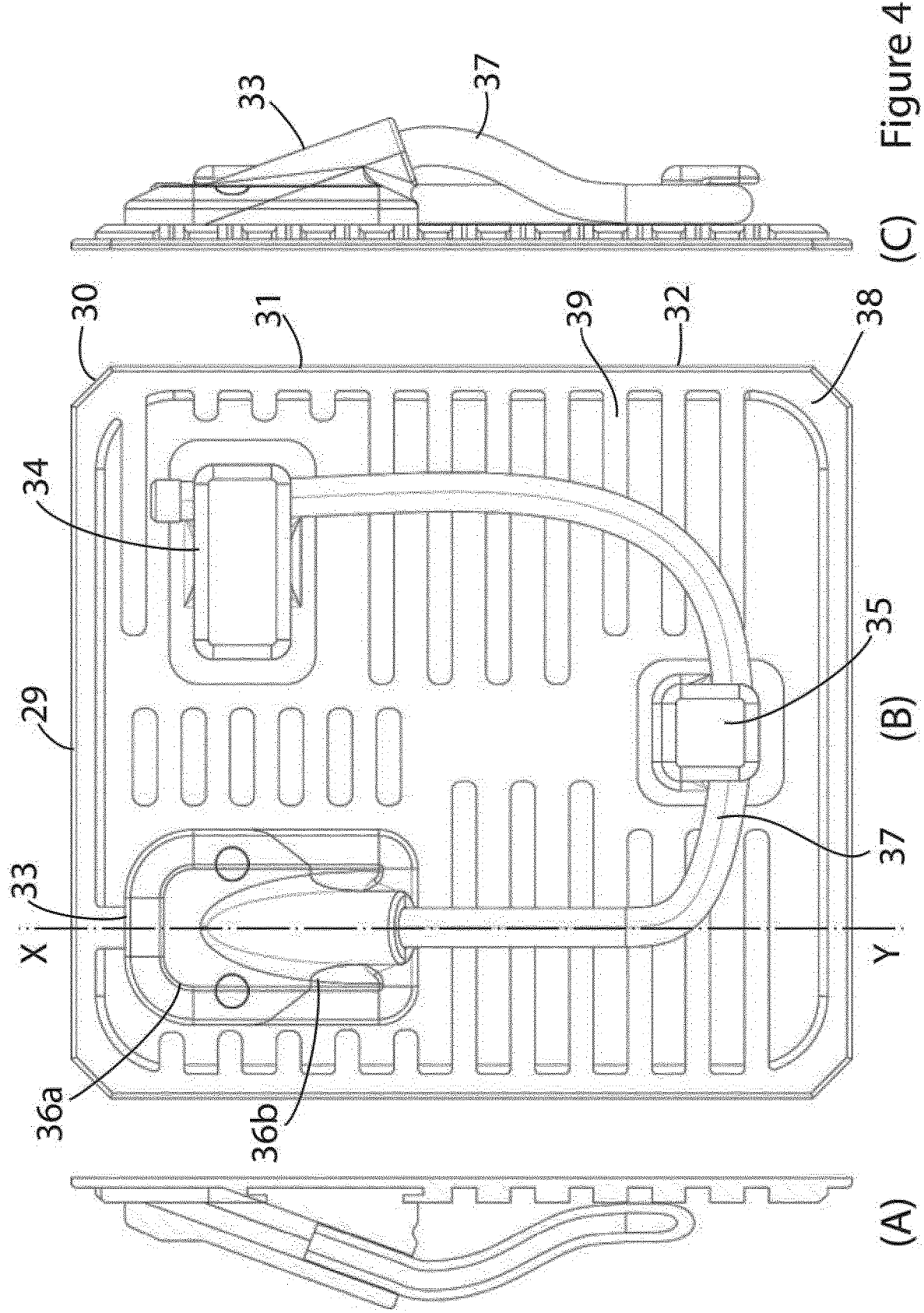
FIG. 4A is a side view of an embodiment of the device of the invention.
FIG. 4B is a front view of an embodiment of the device of the invention.
FIG. 4C is a side view of an embodiment of the device of the invention.

FIG. 4A to C is an illustration of an embodiment of the invention. This embodiment is particularly suited for intravenous lines, chest drains and other smaller French catheters. FIG. 4A is a cross sectional view of the device of 4B through the dashed line from X to Y. FIG. 4C is a side view of the device of FIG. 4B.

Figure 5:
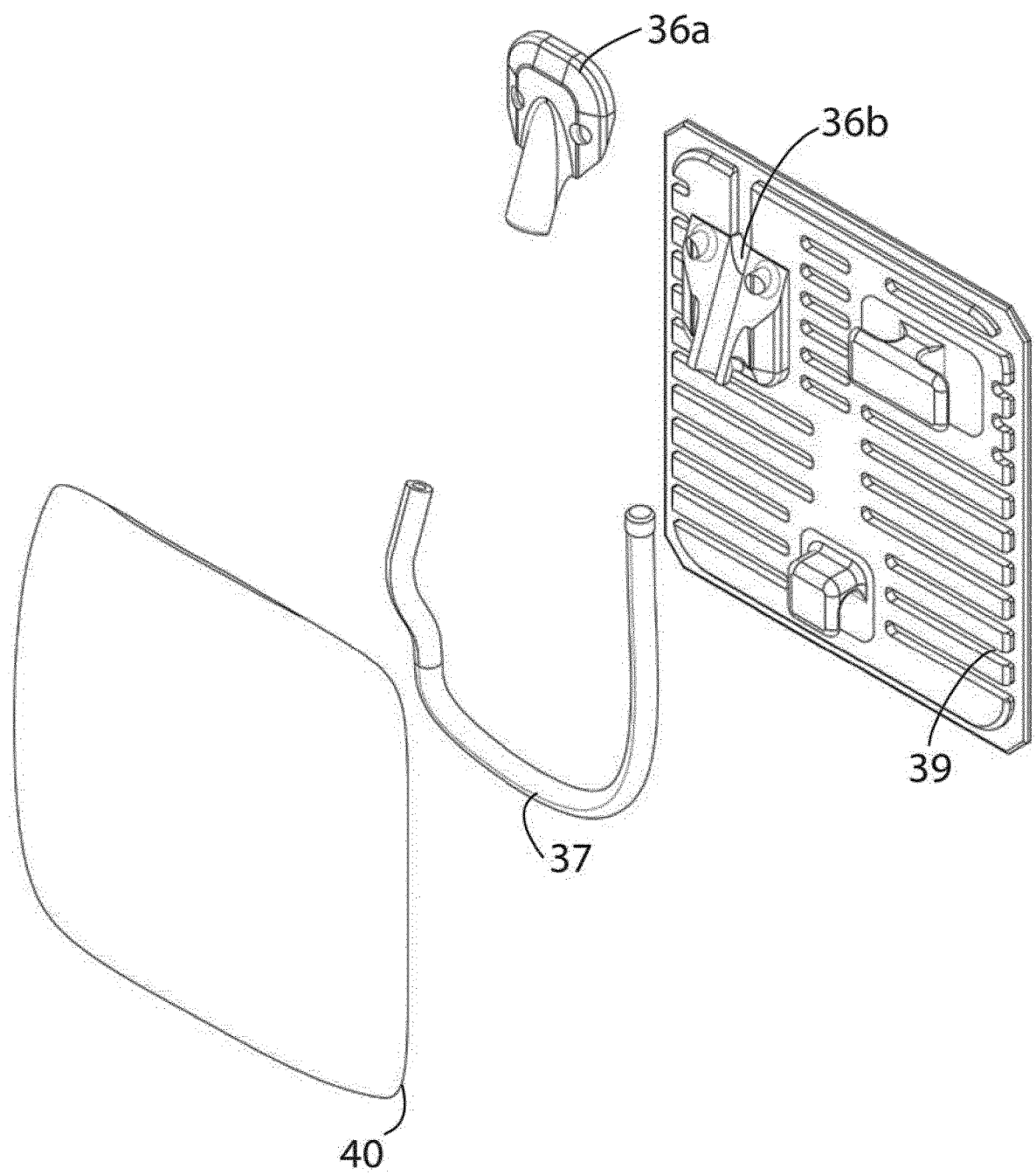
FIG. 5 is an expanded view of the device of FIG. 4.

The device comprises a substantially square shaped base 29 with chamfered edges 30 having a proximal end 31 and a distal end 32. The device has an adhesive backing 38. The proximal end 31 comprises a lock retainer 33 and a passive fit retainer 34. The distal end comprises a passive fit retainer 35. The retainer 35 is a resilient channel. The lock retainer is positioned over an opening to receive a tube. In this embodiment, the lock retainer comprises two interlocking members 36a, 36b, configured to lock the tube 37 therein. The first interlocking member 36b comprises a base comprising a first channel having a sloped top surface and for accommodating at least a portion of the catheter tube. The second interlocking member or cap portion 36a comprises a corresponding second channel engageable with said first channel to lock the tube therein (not shown). The planar body comprises a plurality of spaced apart and parallel slits or apertures 39. These increase the flexibility and conformity of the planar body. FIG. 5 is an expanded view of the device of FIG. 4. The first channel having a sloped top surface 36b is illustrated here. The device comprises a cover member 40.

Another embodiment of the invention is illustrated by FIGS. 6 to 15. Referring to these Figures, there is illustrated a further embodiment(s) in which parts or steps described with reference to the previous embodiment(s) are assigned the same numerals.

Figure 6:
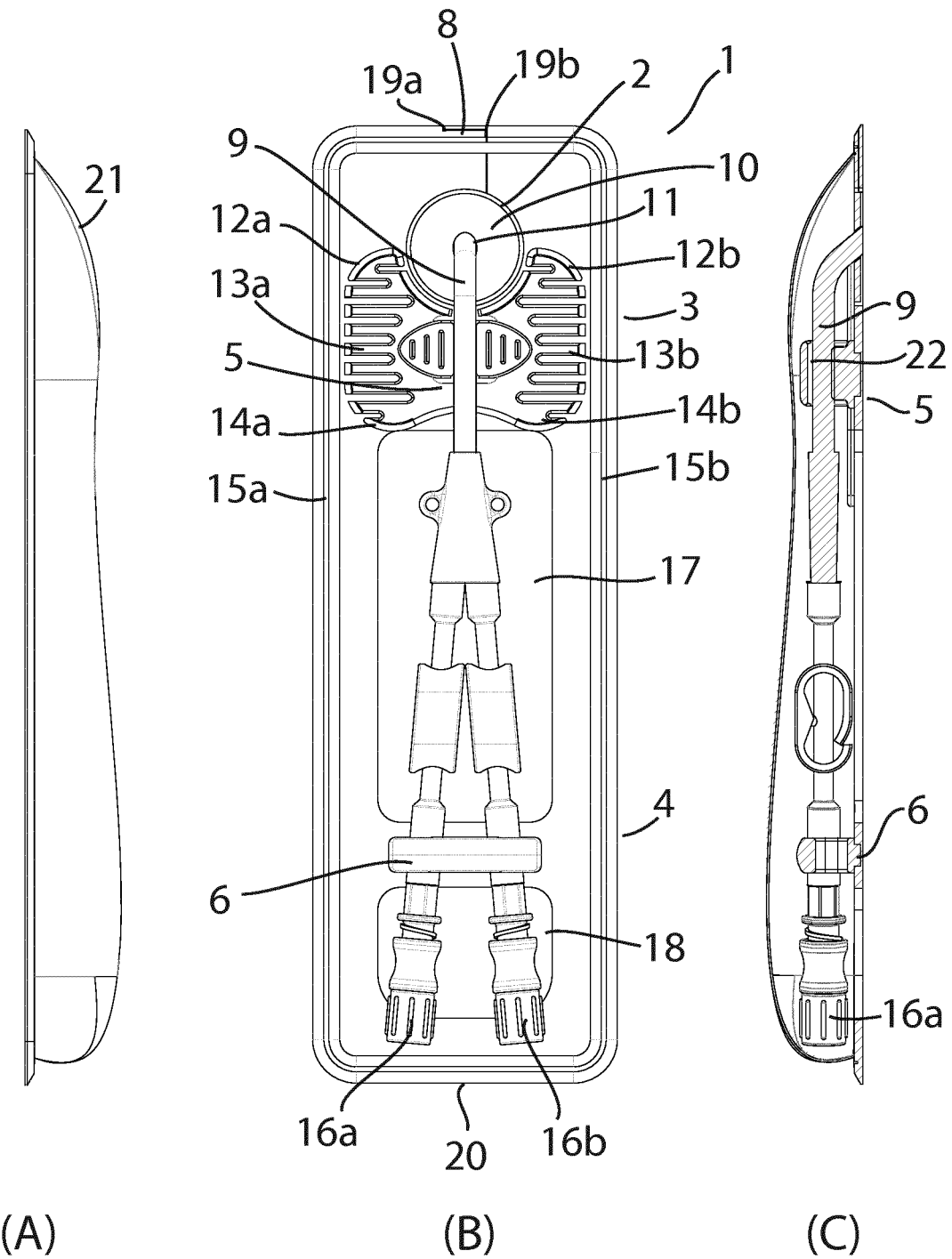
FIG. 6A is a side view of an embodiment of the device of the invention.
FIG. 6B is an plan view of an embodiment of the device of the invention.
FIG. 6C is a side view of an embodiment of the device of the invention.
Figure 7:
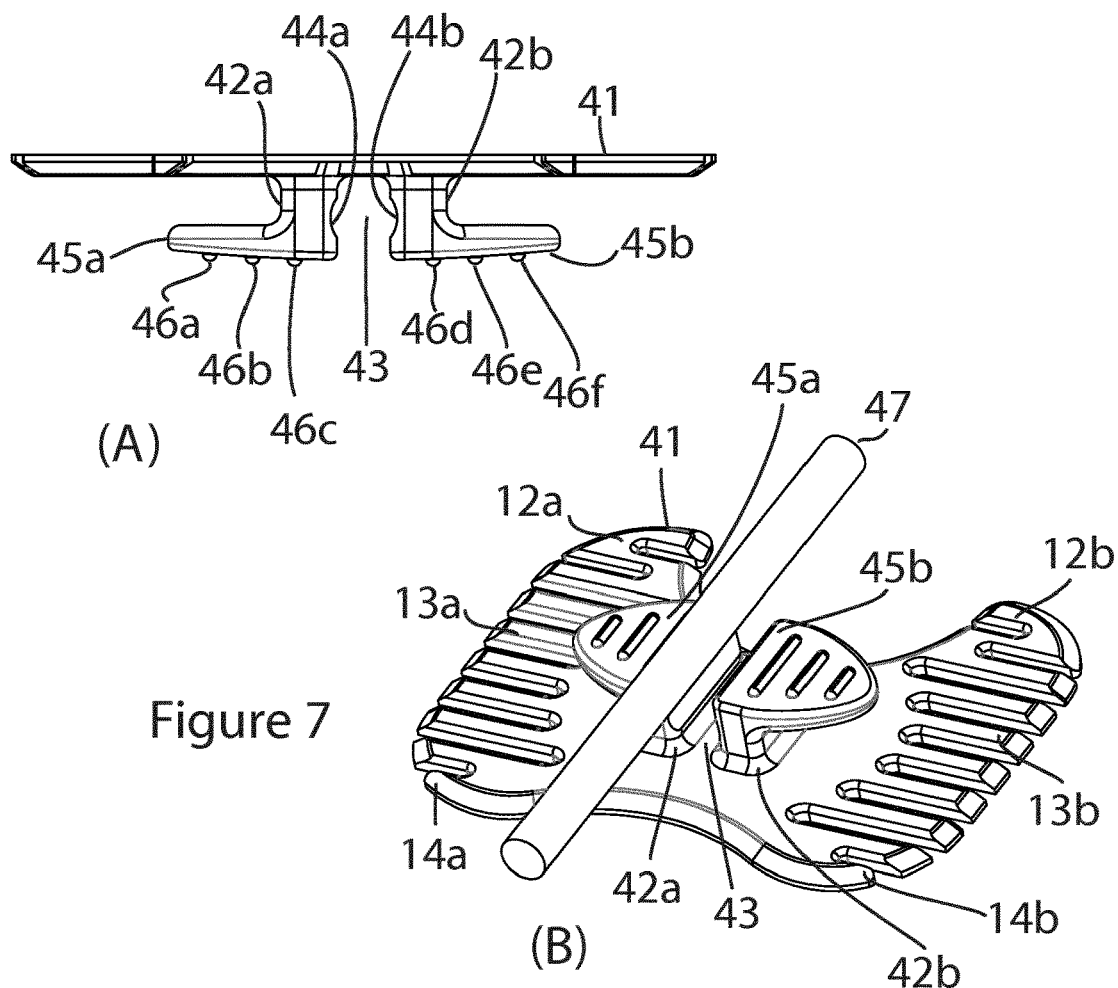
FIG. 7A is a side view of the lock retainer of the device of FIG. 6.
FIG. 7B is a perspective view of the lock retainer of FIG. 7A.
Figure 8:
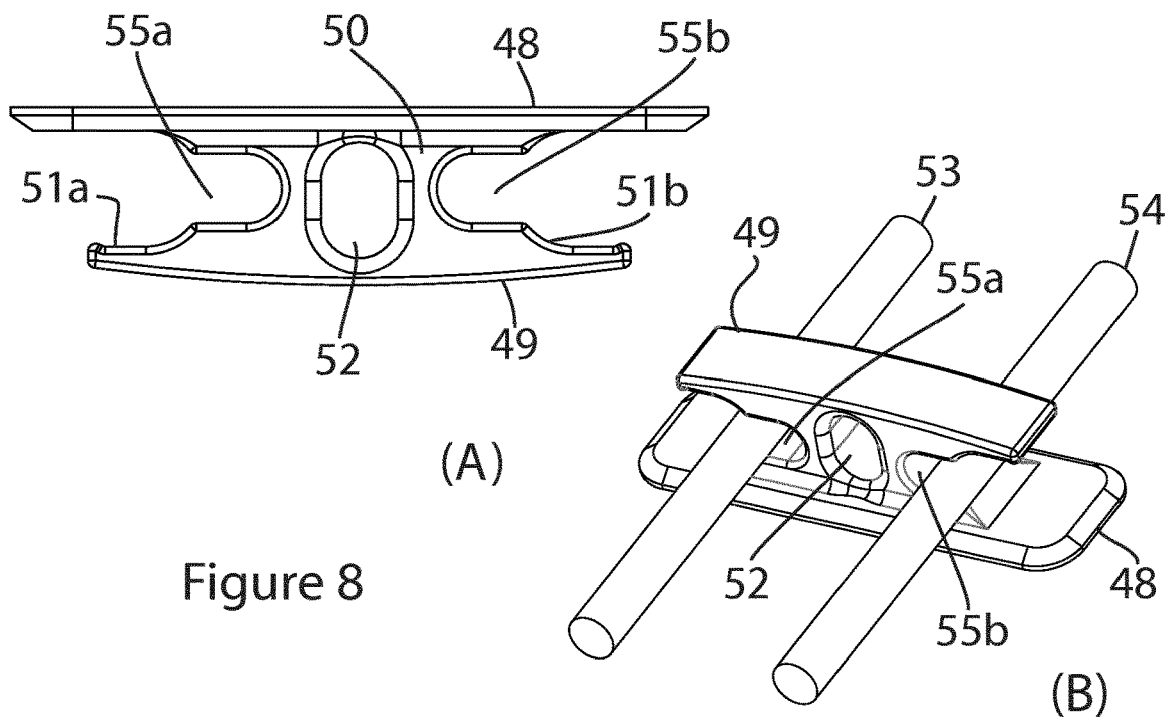
FIG. 8A is a side view of the passive retainer of the device of FIG. 6.
FIG. 8B is a perspective view of the lock retainer of FIG. 8A.

FIG. 6 B is a plan view of the device of an embodiment of the invention. The device comprises an elongated rectangular planar body 1 comprising a flexible silicone-like material.

The body has an adhesive backing (not shown). The adhesive backing attaches the planar body to the skin of the patient (not shown). The planar body comprises a proximal part 3, proximal of the catheter insertion site on the body when in use (not shown) and a distal part 4, distal of the insertion site. An access channel 8 in the form of a radial slit with overlapping edges (19a, 19b) extends from the top edge of the proximal part 3 towards the centre of the planar body terminating in an opening 2 for receiving and accommodating at least part of a catheter tube 9. An antimicrobial patch 10 is placed in the opening. The patch is substantially the same size and shape as the opening. The antimicrobial patch 10 comprises a central aperture 11 for receiving the catheter tube 9. In use, the catheter tube 9 is threaded through the aperture 11 on the patch 10 and the patch 10 is attached to the skin of the patient overlaying the insertion site (not shown). The device is fixed to the body of the patient as outlined in relation to FIG. 1.

The proximal part 3 further comprises a lock retainer 5 configured to lock or secure the catheter tube in place at the insertion site. The lock retainer 5 of the embodiment of FIG. 1 comprises a base and two opposing walls forming a longitudinal channel there between (not shown). The walls form a channel into which the catheter tube 9 is nested. An arm extends from the top surface of each wall. The arms are parallel to the planar body. As illustrated in this Figure, the arms extend in opposite directions. In use, the retainer is accessed by applying force to the cantilevered arms which, when depressed, spreads the channel open to allow the catheter to be place inside the channel. In use, the channel exerts a radial mechanical force inwards once the catheter is placed in the channel and this retains the catheter in all directions, i.e. in the longitudinal, lateral and transverse direction.

The device also comprises a plurality of elongate reinforcing fingers, e.g. 12a, 12b, 13a, 13b, 14a, 14b. The device comprises two sets of opposing reinforcing fingers, one on each side of the lock retainer. The fingers are disposed on the proximal end and extend outwards from the lock retainer towards the outer edge 15a, 15b of the planar body 1. The lock retainer 5 is spaced apart from a passive retainer 6 positioned distal of the insertion site on the distal part 4 of the body. The passive retainer 6 comprises a base and a T-shaped flange extending upwards from the base. The flange forms opposing channels with the base (not shown). The catheter tubes adjacent to the catheter hub 16a, 16b, are retained in the opposing channels. The planar body 1 further comprises an aperture 17 extending between the lock retainer 5 and the friction fit retainer 6. The planar body 1 comprises another aperture 18 extending between the friction fit retainer 6 and the lower edge of the distal part 20.

FIG. 6 A illustrates a side view of the device of FIG. 6B comprising a cover 21. The cover 21 is positioned over the entire top surface of the planar body to enclose the planar body therein. The cover is attached to the planar body along the entire perimeter of the body.

FIG. 6C illustrates a side cross-sectional view of the device of FIG. 6B comprising a transparent cover 21. The cover is positioned over the entire top surface to enclose the planar body therein. The cover is attached along the entire perimeter of the planar body. The catheter tube 9 inserted into the channel 22 of the lock retainer 5 is illustrated by FIG. 6B.

FIG. 7A is a side view of the lock retainer of FIG. 6. The lock retainer comprises a base 41, which extends into a plurality of opposing reinforcing fingers (e.g. 12a, 12b, 13a, 13b, 14a, 14b) on its outer edge (shown in FIG. 7B). The base comprises two upstanding walls 42a, 42b, extending from the base. A longitudinal channel 43 is formed between the walls. As illustrated in FIG. 7A, the walls comprise a groove 44a, 44b, into which the catheter tube can sit when retained in the channel. The shape of the groove is complementary to the shape of the catheter tubing.

Each wall comprises an arm 45a, 45b, extending outwards and parallel to the base. The top surface of the arm comprises three spaced apart ridges, 46a to 46f. The ridges allow the user to grip the arms in order to apply force to move the arms to access the channel.

FIG. 7B is a perspective view of the lock retainer of FIG. 7A, in which a catheter tube 47 is being place inside the longitudinal channel 43.

FIG. 8A is a side view of the passive retainer of FIG. 6. The passive retainer comprises a base 48. The base 48 comprises a T shaped flange 49 extending upwards from the base 48 and which is composed of a wall 50 having two opposing arms 51a, 51b, extending from the top surface of the wall in opposite directions. The flange 49 and the base 48 form two channels 55a, 55b, therebetween, configured to retain the catheter tube therein. The wall 50 of the retainer comprises a central aperture 52. FIG. 8B is a perspective view of the passive retainer of FIG. 8A in which two parts of catheter tubing 53, 54, are retained in the channels 55a, 55b, of the passive retainer.

Figure 9:
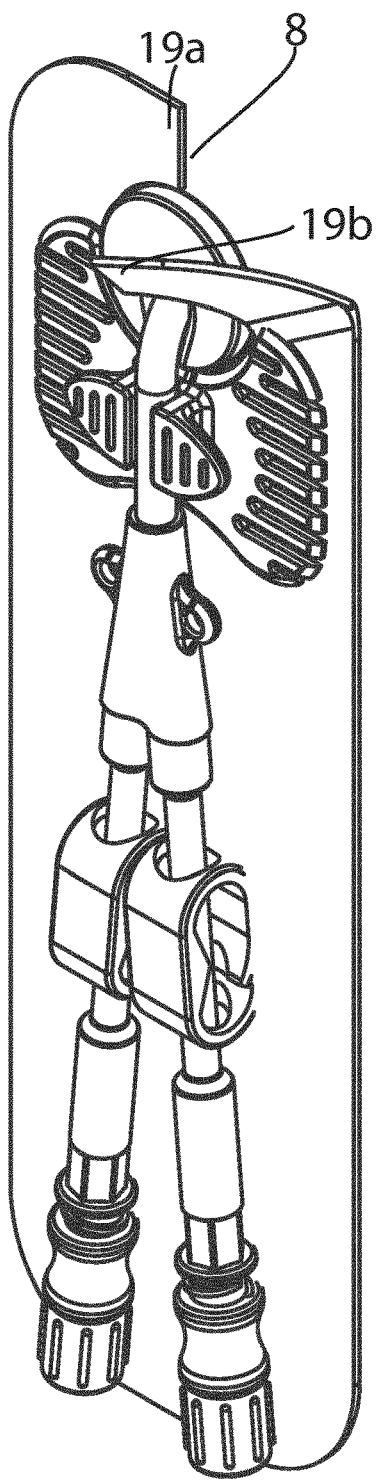
FIG. 9 is a perspective view of the device of FIG. 6.

FIG. 9 is a perspective view of the device of FIG. 6. This figure illustrates how a user accesses the access channel. The access channel 8 is in the form of a radial slit with overlapping edges (19a, 19b). In order to fix the device to the patient, the user pulls apart the edges of the access channel 19a and/or 19b. In this embodiment, the user has moved channel edge 19b downwards and towards the user. The catheter tube can then be slidably received through the channel and into the opening. The edge 19b can then be returned to its original position to allow the device to be fixed to the body of the patient (not shown).

Figure 10:
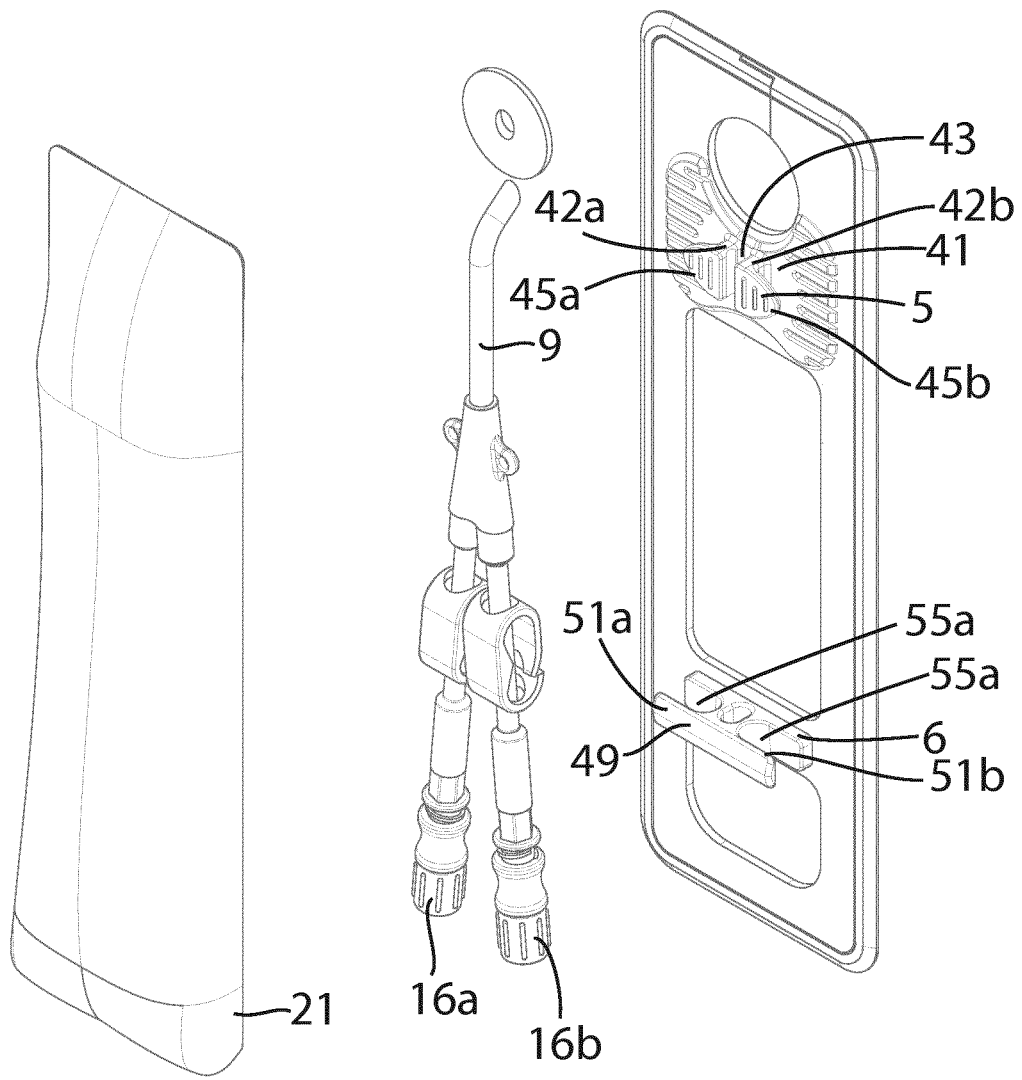
FIG. 10 is an expanded view of the device of FIG. 6.

FIG. 10 is an expanded view of the device of FIG. 6.

Figure 11:
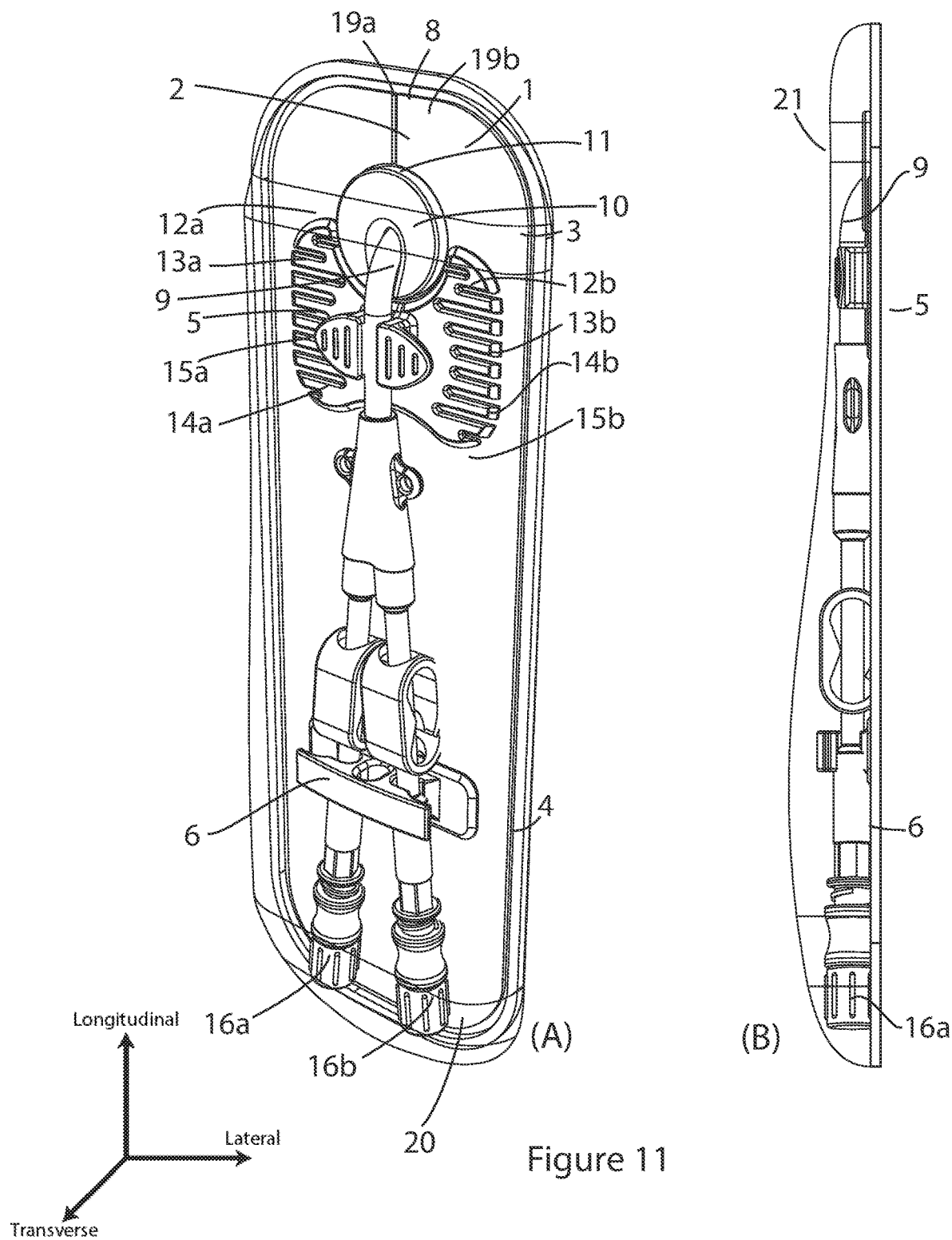
FIG. 11A is a perspective view of the device of FIG. 6.
FIG. 11B is a side view of the device of FIG. 11A.

FIG. 11 A is a perspective view of the device of FIG. 6. FIG. 10B is a side view of the device of FIG. 11A. In this figure, the tubing within the channels of the retainer is illustrated.

Figure 12:
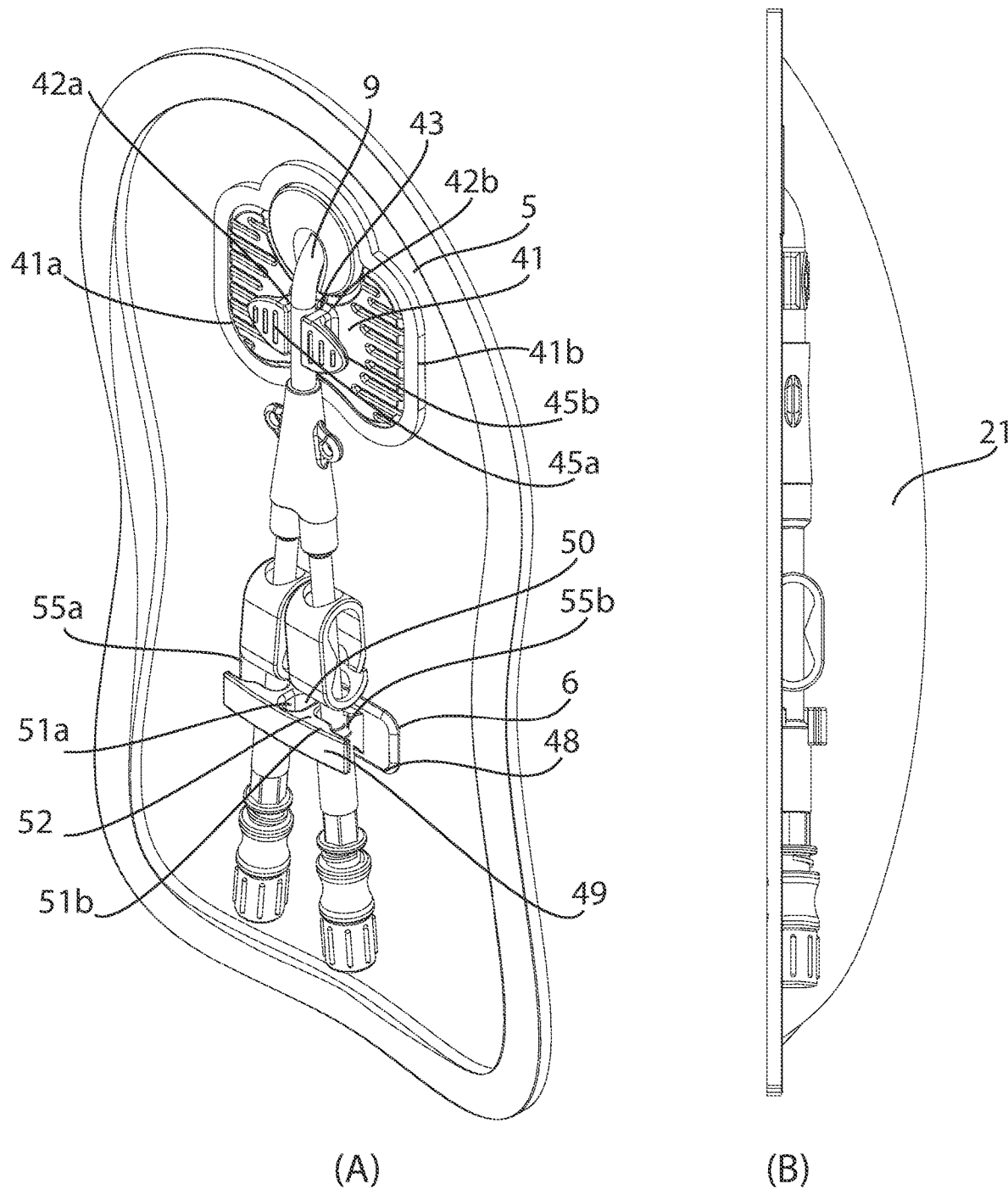
FIG. 12A is a perspective view of an embodiment of the device of the invention.
FIG. 12B is a side view of the device of FIG. 12A.
Figure 13:
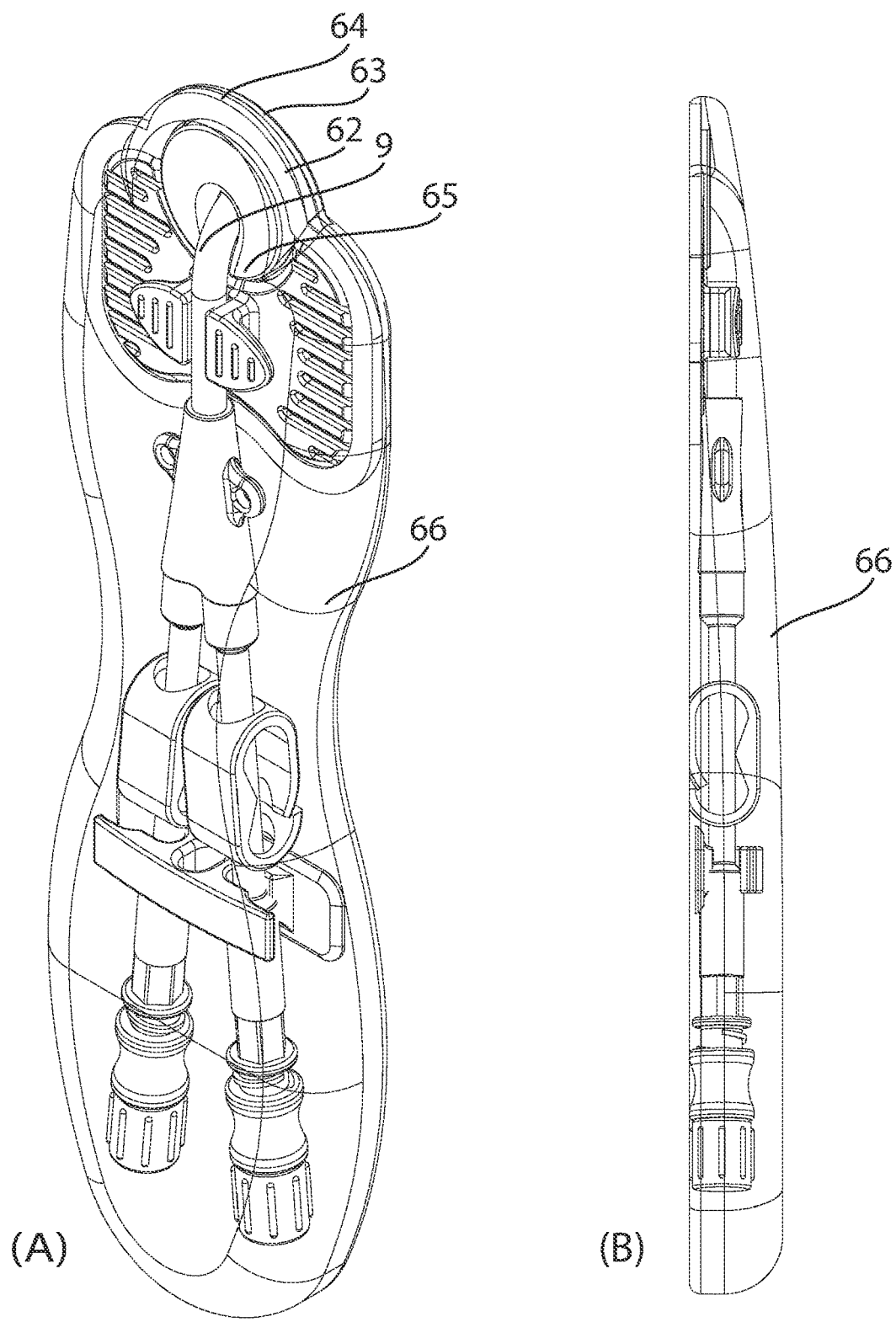
FIG. 13A is a perspective view of an embodiment of the device of the invention.
FIG. 13B is a side view of the device of FIG. 13A.

An embodiment of the device assembly is illustrated by FIGS. 12 A and B. The device of FIG. 12A comprises a lock retainer 5 located directly adjacent to the insertion site of the catheter 9 on the patient (not shown). Surrounding the catheter 9 at the insertion site is an antimicrobial patch 10. The lock retainer 5 comprises a planar body or base 41. The lock retainer is a single moulded piece. The edges of the base 41a, 41b, have a plurality of reinforcing fingers. There are nine reinforcing fingers on the first edge 41a and nine reinforcing fingers on the second edge 41b. The lock retainer 5 comprises two opposing upstanding walls 42a, 42b, forming a longitudinal channel 43 there between. The catheter tubing is nested in the channel. The inner surface of the walls forming the channel 43 comprises a groove into which the catheter tubing can sit. This groove may have a cylindrical profile to complement that of the tubing. An arm extends from the top surface of each wall (45a, 45b). The arms are parallel to the planar body. As illustrated in this Figure, the arms 45a, 45b, extend in opposite directions. In use, the retainer is accessed by applying force to the cantilevered arms which, when depressed, spreads the channel open to allow the catheter to be place inside the channel. In use, the channel exerts a radial mechanical force inwards once the catheter is placed in the channel and this retains the catheter in all directions, i.e. in the longitudinal, lateral and transverse direction. The top edge of the base of the lock retainer, i.e. that proximal to the insertion site, is shaped so that the lock retainer can be located as close to the insertion site as possible. In this instance, the profile of the edge is such that its shape is complementary to the circular shape of the edge of the antimicrobial patch.

The assembly of FIG. 12 also comprises a passive retainer. In this embodiment, the passive retainer 6 is separate from the lock retainer, i.e. it is not located on the same flexible planar body. The passive retainer 6 is disposable or attachable to the patient's body at a position distal, and spaced-apart, from the lock retainer. The passive retainer comprises a base 48. The base 48 comprises a T shaped flange 49 extending upwards from the base 48 and which is composed of a wall 50 having two opposing arms 51a, 51b, extending from the top surface of the wall in opposite directions. The flange 49 and the base 48 form a channel 55a, 55b, there between configured to retain the catheter tube therein. The wall 50 of the retainer comprises a central aperture 52.

The device assembly comprises a cover 21 that is configured to attach directly to the body of the patient overlaying the device assembly. The cover is semipermeable and transparent.

An embodiment of the device assembly is illustrated by FIGS. 13A and 13B. This embodiment is similar to the embodiment of FIG. 12 with the exception that an adhesive surround 62 frames the edge of the lock retainer. The adhesive surround may be silicone or silicone like material, a hydrocolloid or a polyurethane foam. The top edge of this adhesive 63 comprises an access channel 64 which terminates in an opening 65 for accommodating the catheter tube 9. The device assembly comprises a cover in the form of a semipermeable and transparent bag 66. The bag completely surrounds the device assembly. The retainers are attached to the bag via an adhesive on a surface of the bag, such as the under-surface of the bag or part thereof and, in turn, the bag is attached to the body of the patient. The bag 66 is flexible and the insertion and adherence of the device provides a flat surface.

FIG. 14A to C are views of an embodiment of a passive retainer of an embodiment of the device of the invention. The retainer of FIG. 14A comprises a base 56 comprising two opposing upstanding walls, 57a, 57b. The top end of each wall comprises an arm 58a, 58b, extending parallel to the base. The arms 58a, 58b, are opposing and extend inwards towards the centre of the base. A channel 59a is formed between the base 56 and the arm of the wall 57a. A similar channel 59b is formed between the base 56 and the arm of the wall 57b. This channel(s) is configured to retain part of a catheter tube therein. This is illustrated by FIG. 14C in which tube 60, 61, are retained in the channels 59a, 59b, respectively.

FIG. 14D to F are views of the passive retainer as illustrated by FIGS. 8A and 8B.

FIG. 15A is a perspective view of a device of the invention. The device is equivalent to that of FIG. 12A with the exception that the lock retainer 5 is disposed or attached to a flexible planar body 67 (e.g. a small adhesive back pad) and the passive retainer 6 is disposed or attached to a flexible planar body 68 (e.g. a small adhesive back pad) The planar bodies are adhesive backed for attachment to the patient's body.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A device assembly for securing a catheter to the skin of a patient, the device comprising:
   a clamp configured to be attached to the skin of a patient directly adjacent to an insertion site of a catheter and to retain a catheter tube therein in a fixed position with respect to the skin of the patient,
   a passive retainer configured to retain a catheter tube therein preventing movement of the catheter tube in a lateral and transverse direction and attachable on the skin of a patient distal to the insertion site, and spaced-apart from the clamp,
   wherein the clamp is separate from the passive retainer, and
   wherein the passive retainer is configured to retain the catheter tube therein without preventing movement of the catheter tube in a longitudinal direction through the passive retainer.

2. The device assembly of claim 1, further comprising:
   a flexible planar body on which the clamp is disposed,
   wherein the flexible planar body includes a first flexible planar body element and a second flexible planar body element.

3. The device assembly of claim 1, wherein the passive retainer includes one of an interference fit retainer, a friction fit retainer, a hook, a pin, a moulded living spring, and a resilient channel, and
   wherein the passive retainer is T-shaped.

4. The device assembly of claim 2, further comprising:
   an antimicrobial patch or pad configured for attachment to the body over the catheter insertion site and surrounding the catheter at the insertion site.

5. The device assembly of claim 2, wherein the flexible planar body elements comprise one of silicone, a silicone-like material, and polyurethane.

6. The device assembly of claim 2, wherein the flexible planar body elements are bilaterally flexible.

7. The device assembly of claim 1, further comprising:
   a removable cover, wherein the cover is semipermeable or transparent.

8. The device assembly of claim 2, further comprising:
   at least one reinforcing finger disposed on the planar body, the clamp or the passive retainer.

9. The device assembly of claim 1, further comprising:
   an additional passive retainer.

10. The device assembly of claim 2, wherein an attachment surface of each of the first flexible planar body element and second flexible planar body element comprises an adhesive for attachment to the skin of a patient.

11. The device assembly of claim 4, wherein the antimicrobial patch or pad comprises or is impregnated with, chlorhexidine gluconate, iodine or silver alginate or any suitable agent for reducing local infections, catheter-related blood stream infections (CRBSI) and skin colonization of microorganisms commonly associated with CRBSI.

12. The device assembly of claim 1, wherein the passive retainer includes at least one laterally extending arm configured to prevent removal of the catheter tube from the passive retainer in the transverse direction.

13. The device assembly of claim 1, wherein the passive retainer includes
   a top portion forming a pair of laterally extending and opposing arms for receiving the catheter tube into the passive retainer in a lateral direction, and
   an opening at the top portion of the passive retainer for receiving the catheter tube into the passive retainer in a transverse direction.

14. A method of securing a catheter to a patient, the method comprising:
   using a device assembly for securing a catheter to the skin of the patient, the device assembly including:
      a clamp configured to be attached to the skin of the patient directly adjacent to an insertion site of a catheter and to retain a catheter tube therein in a fixed position with respect to the skin of the patient; and
      a passive retainer configured to retain a catheter tube therein preventing movement of the catheter tube in a lateral and transverse direction and attachable to the skin of the patient distal to the insertion site, and spaced apart from the clamp,
      wherein the clamp is separate from the passive retainer; and
      wherein the passive retainer is configured to retain the catheter tube therein without preventing movement of the catheter tube in a longitudinal direction through the passive retainer,
   attaching the clamp on the body of the patient 1 mm to 40 mm from the catheter insertion site;
   clamping a proximal end of the catheter with the clamp;
   attaching the passive retainer distal to the insertion site, and spaced-apart from the clamp on the patient's body; and
   inserting a distal end of the catheter into the passive retainer.

15. The method of claim 14, further comprising:
   applying an antimicrobial patch or pad on the patient's skin and around the catheter tube at the insertion site.

16. A device assembly for securing a catheter to the skin of a patient, the device comprising:
   a clamp configured to be attached to the skin of a patient directly adjacent to an insertion site of a catheter and to retain a catheter tube therein in a fixed position with respect to the skin of the patient,
   a passive retainer attachable on the skin of a patient distal to the insertion site, and spaced-apart from the clamp, the passive retainer including a base and a top portion together forming a pair of laterally extending channels for receiving the catheter tube into the passive retainer in a lateral direction, retaining the catheter tube, and preventing removal of the catheter tube in the transverse direction, and
   wherein the clamp is separate from the passive retainer.

17. The device assembly of claim 16, wherein the top portion includes a pair of laterally extending and opposing arms.

18. The device assembly of claim 17, wherein each of the channels include portions of varying diameters capable of securing catheter tubes of different diameters.

19. The device assembly of claim 18, wherein the passive retainer further includes a transverse channel extending from the top portion, the transverse channel located between the opposing arms and allowing entry of the catheter tube in the transverse direction.

* * * * *